US007378538B2

(12) United States Patent
Nagase et al.

(10) Patent No.: US 7,378,538 B2
(45) Date of Patent: May 27, 2008

(54) COMPOUND HAVING PHOSPHORYLCHOLINE GROUP, POLYMER THEREOF AND PROCESS FOR PRODUCING THE SAME

(75) Inventors: Yu Nagase, Hiratsuka (JP); Masataka Oku, Hiratsuka (JP); Kazuhiko Ishihara, Mitaka (JP); Yasuhiko Iwasaki, Tama (JP)

(73) Assignee: Tokai University, Tokyo (JP)

( * ) Notice: Subject to any disclaimer, the term of this patent is extended or adjusted under 35 U.S.C. 154(b) by 455 days.

(21) Appl. No.: 10/518,462

(22) PCT Filed: Feb. 18, 2004

(86) PCT No.: PCT/JP2004/001794

§ 371 (c)(1),
(2), (4) Date: Dec. 22, 2004

(87) PCT Pub. No.: WO2004/074298

PCT Pub. Date: Sep. 2, 2004

(65) Prior Publication Data

US 2006/0041160 A1     Feb. 23, 2006

(30) Foreign Application Priority Data

Feb. 18, 2003    (JP)    ............... 2003-040154

(51) Int. Cl.
*C07F 9/02*    (2006.01)
(52) U.S. Cl. ............... 558/169; 558/170; 558/166
(58) Field of Classification Search ............... 558/169, 558/170, 166
See application file for complete search history.

(56) References Cited

U.S. PATENT DOCUMENTS 5,591,882 A    1/1997    Straford et al.
6,040,415 A *    3/2000    Arimori et al. ............... 528/71

FOREIGN PATENT DOCUMENTS

EP    0574355 A1    12/1993
EP    0767212 A1    4/1997
WO    WO 93/01221 A1    1/1993

OTHER PUBLICATIONS

Kazuhiko Ishihara (1999) "New Development of Nonthrombogenic Materials," *Surgery* 61(2), 4 pages.
Kazuhiko Ishihara (1990) "Preparation of Phospolipid Polymers and Their Properties as Polymer Hydrogel Membranes," *Polymer Journal* 22(5), pp. 355-360.
Kazuhiko Ishihara (2000) "Bioinspired Phospholipid Polymer Biomaterials for Making High Performance Artificial Organs," *Science and Technology of Advanced Materials I*, pp. 131-138.
Kazuhiko Ishihara (2000) "New Polymeric Biomaterials-Phospholipid Polymers with a Biocompatible Surface," *Frontiers Med. Biol. Enging.* 10(2), pp. 83-95.
European Search Report mailed on Oct. 12, 2006 for European Patent Application No. EP 04 71 2183. 3 pages.

* cited by examiner

*Primary Examiner*—Rei-Tsang Shiao
(74) *Attorney, Agent, or Firm*—Morrison & Foerster LLP

(57) ABSTRACT

A compound of the invention is a specific compound having a phosphorylcholine group, and a polymer of the invention comprises at least 1 mol % of repeating units with a phosphorylcholine group and has a number-average molecular weight of 1,000 or more, the repeating units with a phosphorylcholine group being represented by the formula (II):

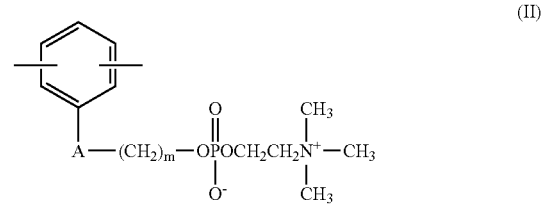

wherein A is a bond selected from a single bond, —O—, —COO—, —OOC—, —CONH—, —NH—, —NHCO—, —$NR^2$— and —$CH_2O$— where $R^2$ is an alkyl group having 1 to 6 carbon atoms; and m is an integer of 1 to 12.

5 Claims, 7 Drawing Sheets

COMPOUND HAVING PHOSPHORYLCHOLINE GROUP, POLYMER THEREOF AND PROCESS FOR PRODUCING THE SAME

This application is a 371 of PCT/JP04/01794 filed on Feb. 18, 2004.

FIELD OF THE INVENTION

The present invention relates to a novel compound having a phosphorylcholine group, a novel polymer with a phosphorylcholine side group that is obtained by polymerization using the compound as a monomer, and a process for producing the polymer.

BACKGROUND OF THE INVENTION

It is a known fact that living organisms react defensively against implanted artificial organs or medical devices to show prominent rejections such as blood coagulation, inflammation and encapsulation. This is a result of a series of bioactivation reactions that start from adsorption of proteins on materials constituting the artificial organs and medical devices. Accordingly, treatments with such artificial organs or medical devices entail simultaneous use of drugs, for example anticoagulants such as heparin and immunosuppressants.

However, side effects of these drugs have been concerned when the treatment extends over a long period of time or as the patients grow older.

Thus, development is under way for a series of medical materials capable of solving such problems, known as biocompatible materials. Of the biocompatible materials developed so far, 2-methacryloyloxyethyl phosphorylcholine (MPC) homopolymers and copolymers with other monomers (hereinafter "MPC polymers") show particularly remarkable biocompatibility (Ishihara et al., Polymer Journal, Vol. 22, p. 355, 1990). These polymers are developed focusing on the structure of biomembrane surfaces such that they have phosphorylcholine groups which are phospholipid polar groups.

MPC, which is a methacrylate, is water soluble as a homopolymer and can be rendered water insoluble by copolymerization with other vinyl monomers to attain suitable structures for surface treatment of the medical devices.

By coating the device surface with the MPC polymer, blood coagulation can be prevented without giving the anticoagulant, and subcutaneous implementation tests have proven very high biocompatibility (Ishihara et al., Surgery, Vol. 61, p. 132, 1999). With such properties, the MPC polymers have been used as surface-coating materials for medical devices already applied in clinical settings in the United States and Europe. The number of approvals given to such coated devices has been increasing also in Japan. These movements have created expectations that medical device effectiveness will be dramatically improved and the patients can enjoy higher quality of life.

However, resistance to heat in autoclave sterilization, hydrolysis resistance and mechanical strength are still insufficient because of the flexible main chain structures of the MPC/vinyl compound copolymers in addition to the MPC's inherent hydrophilicity. There is therefore a need for a new material that exhibits improved heat resistance, hydrolysis resistance and mechanical strength while maintaining superior biocompatibility and processability of the MPC polymers.

DISCLOSURE OF THE INVENTION

The present inventors carried out earnest studies in view of the aforesaid circumstance, and succeeded in synthesizing a specific novel compound having a phosphorylcholine group capable of affording by polymerization a novel polymer excellent in mechanical strength, hydrolysis resistance, heat resistance and biocompatibility. With these findings, the present inventors accomplished the invention.

Thus, the present invention has an object of providing a polymer and a production process thereof, which polymer has improved heat resistance, hydrolysis resistance and mechanical strength while maintaining superior biocompatibility and processability. It is another object of the invention to provide a compound as a starting material for the polymer.

A compound having a phosphorylcholine group according to the present invention is represented by the formula (I):

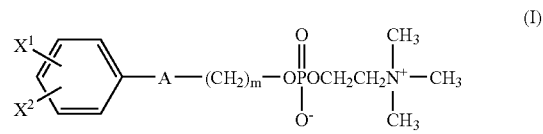

wherein $X^1$ and $X^2$ are both amino groups or —COOR$^1$ groups where R$^1$'s may be the same or different from each other and are each a hydrogen atom or a carboxyl-protective group; A is a bond selected from a single bond, —O—, —COO—, —OOC—, —CONH—, —NH—, —NHCO—, —NR$^2$— and —CH$_2$O— where R$^2$ is an alkyl group having 1 to 6 carbon atoms; and m is an integer of 1 to 12.

The compound having a phosphorylcholine group is preferably a diamine compound in which $X^1$ and $X^2$ are both amino groups.

Also preferably, the compound having a phosphorylcholine group is a dicarboxylic acid compound in which $X^1$ and $X^2$ are both —COOR$^1$ groups where R$^1$'s are both hydrogen atoms.

Further, the compound having a phosphorylcholine group is suitably a dicarboxylic acid compound in which $X^1$ and $X^2$ are both —COOR$^1$ groups where R$^1$'s may be the same or different from each other and are each an alkyl group having 1 to 6 carbon atoms, a substituted or unsubstituted arylmethyl group, a cyclic ether residue, an alkylsilyl group or an alkylphenylsilyl group.

A polymer according to the present invention comprises at least 1 mol % of repeating units with a phosphorylcholine group and has a number-average molecular weight of 1,000 or more, the repeating units with a phosphorylcholine group being represented by the formula (II):

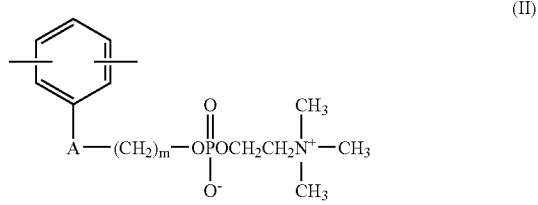

wherein A is a bond selected from a single bond, —O—, —COO—, —OOC—, —CONH—, —NH—, —NHCO—, —NR$^2$— and —CH$_2$O— where R$^2$ is an alkyl group having 1 to 6 carbon atoms; and m is an integer of 1 to 12.

The polymer preferably has one or more bonds selected from an amido bond, an ester bond, a urethane bond, a urea bond and an imido bond within its main chain skeleton.

A process for producing a polymer according to the present invention comprises performing polycondensation or polyaddition of a compound having a phosphorylcholine group represented by the formula (I) and another polymerizable monomer:

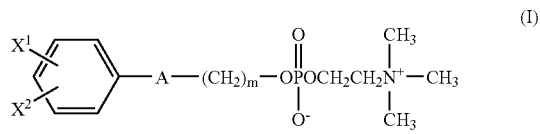
(I)

wherein X$^1$ and X$^2$ are both amino groups or —COOR$^1$ groups where R$^1$'s may be the same or different from each other and are each a hydrogen atom or a carboxyl-protective group; A is a bond selected from a single bond, —O—, —COO—, —OOC—, —CONH—, —NH—, —NHCO—, —NR$^2$— and —CH$_2$O— where R$^2$ is an alkyl group having 1 to 6 carbon atoms; and m is an integer of 1 to 12.

The other polymerizable monomer is preferably one or more monomers selected from a dicarboxylic acid, a dicarboxylic acid derivative, a tetracarboxylic dianhydride, a diisocyanate compound, a diamine compound and a diol compound.

PREFERRED EMBODIMENTS OF THE INVENTION

Figure 1:
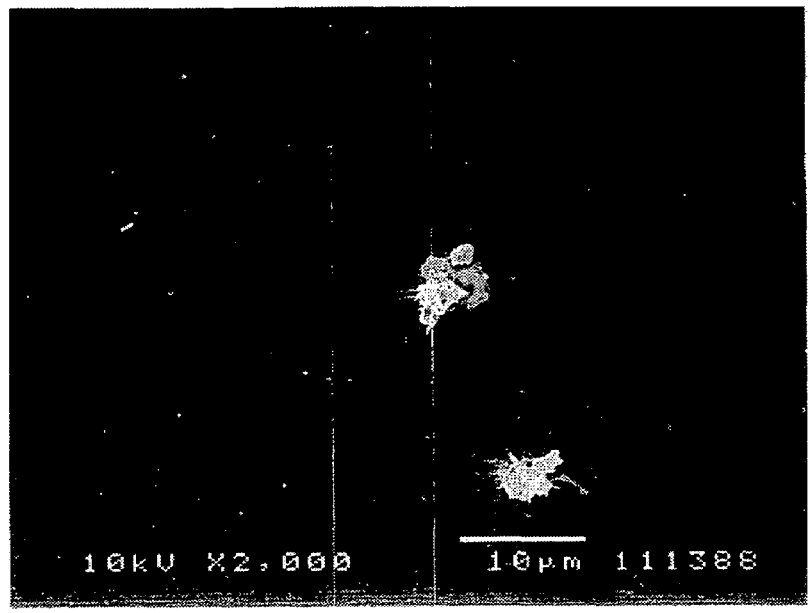
FIG. 1 is an electron micrograph (2000× magnification) showing a PA-1 membrane surface after contact with human PRP.
Figure 2:
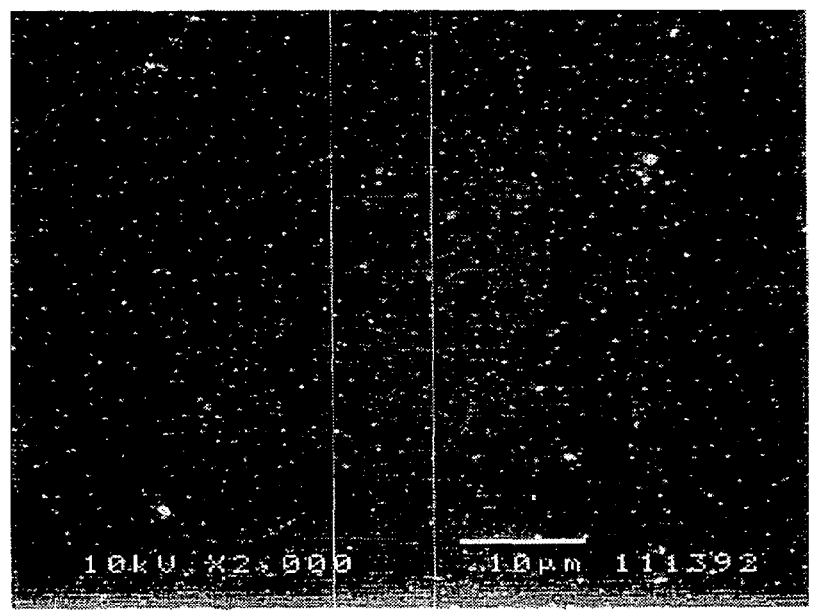
FIG. 2 is an electron micrograph (2000× magnification) showing a PA-2 membrane surface after contact with human PRP.
Figure 3:
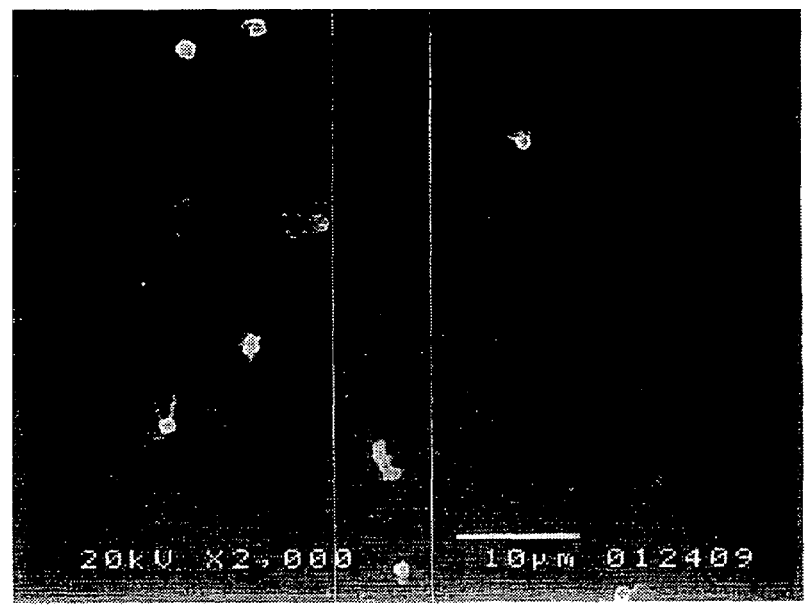
FIG. 3 is an electron micrograph (2000× magnification) showing a PA-3 membrane surface after contact with human PRP.
Figure 4:
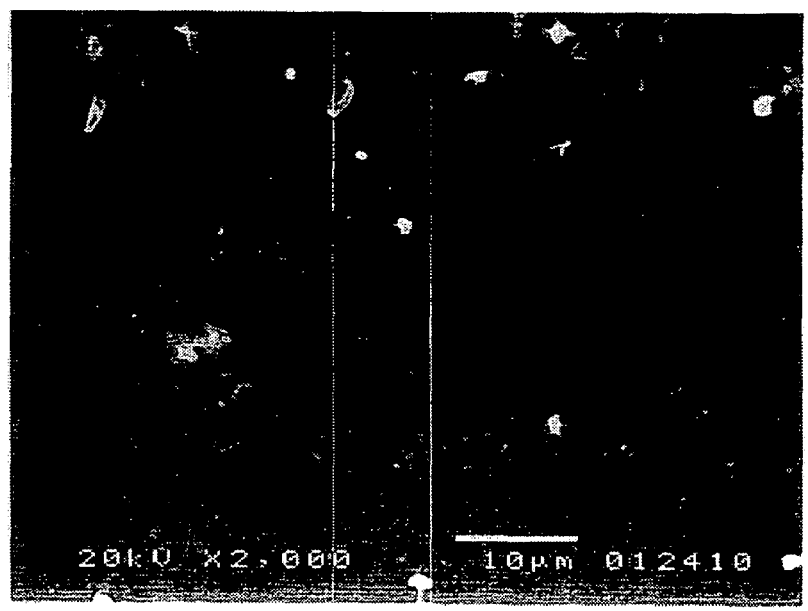
FIG. 4 is an electron micrograph (2000× magnification) showing a PA-4 membrane surface after contact with human PRP.
Figure 5:
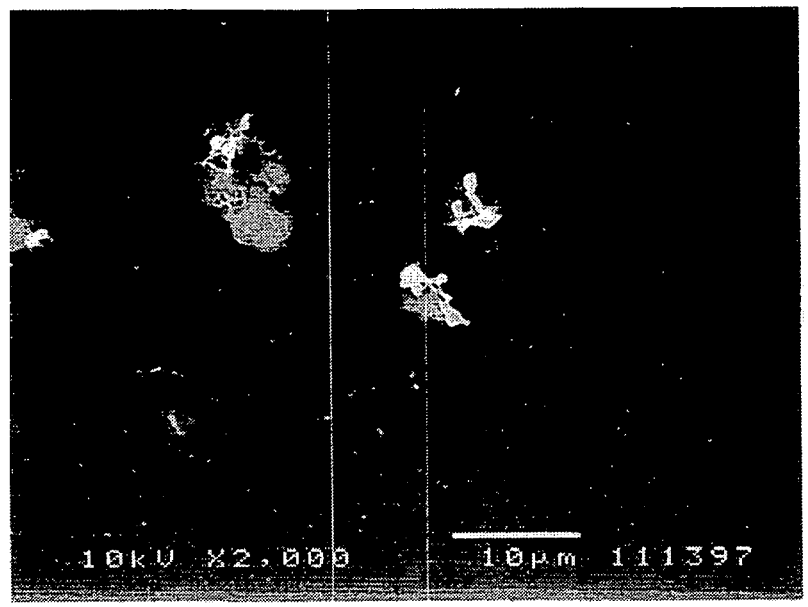
FIG. 5 is an electron micrograph (2000× magnification) showing a PA-5 membrane surface after contact with human PRP.
Figure 6:
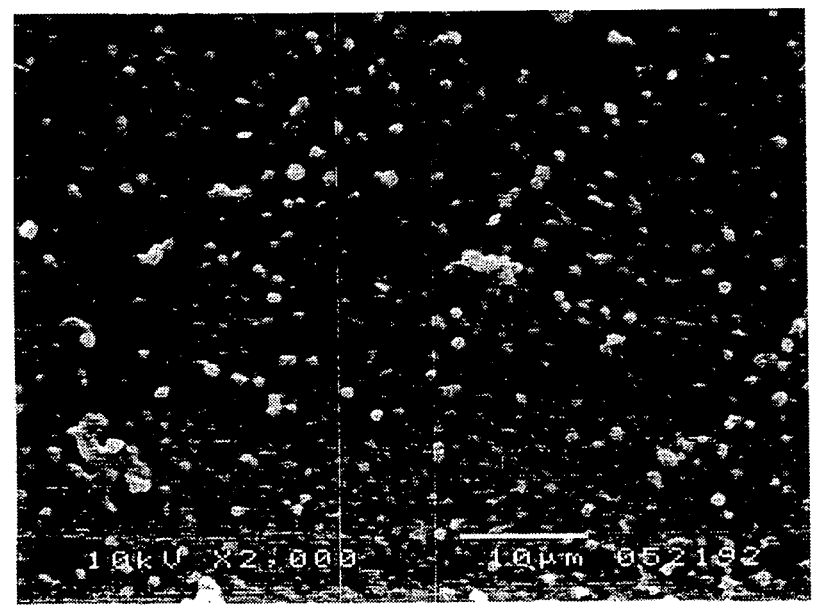
FIG. 6 is an electron micrograph (2000× magnification) showing a PA-6 membrane surface after contact with human PRP.
Figure 7:
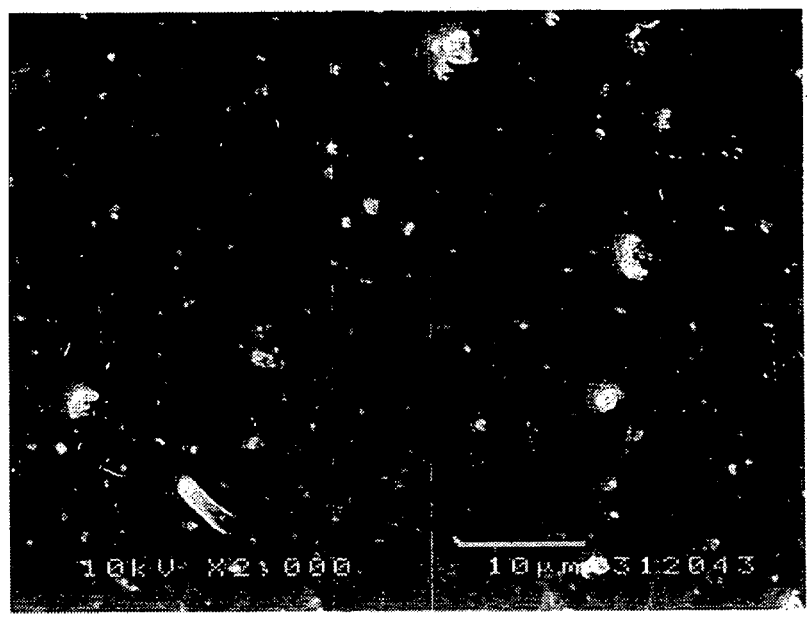
FIG. 7 is an electron micrograph (2000× magnification) showing a PA-7 membrane surface after contact with human PRP.
Figure 8:
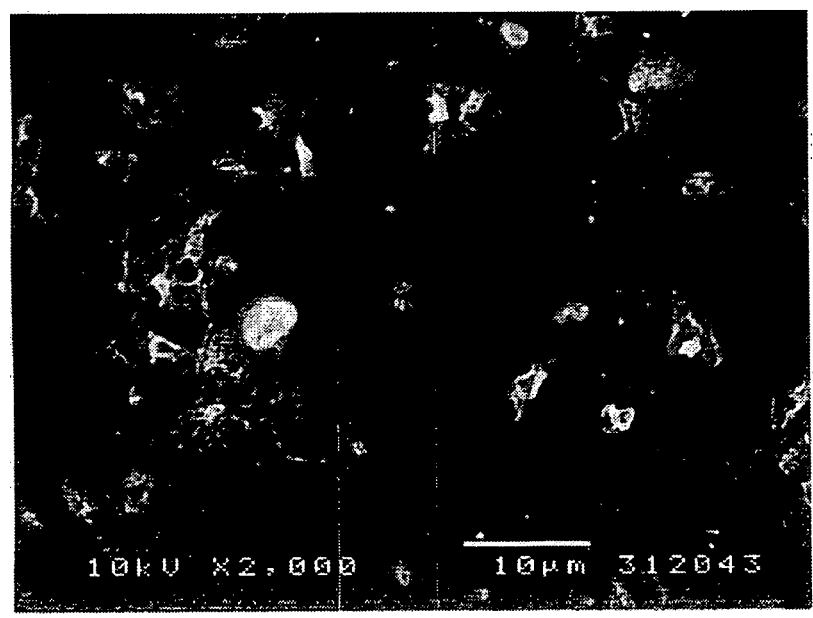
FIG. 8 is an electron micrograph (2000× magnification) showing a PA-8 membrane surface after contact with human PRP.

Hereinbelow, the present invention will be described in detail.

<Compound Having a Phosphorylcholine Group>

The compound having a phosphorylcholine group is represented by the following formula (I):

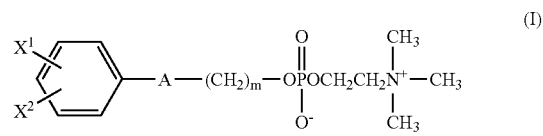
(I)

wherein X$^1$ and X$^2$ are both amino groups or —COOR$^1$ groups where R$^1$'s may be the same or different from each other and are each a hydrogen atom or a carboxyl-protective group; A is a bond selected from a single bond, —O—, —COO—, —OOC—, —CONH—, —NH—, —NHCO—, —NR$^2$— and —CH$_2$O—, and preferably —O— or —COO— where R$^2$ is an alkyl group having 1 to 6 carbon atoms; and m is an integer of 1 to 12, and preferably 1 to 6.

When A in the formula (I) represents —NR$^2$—, the alkyl groups having 1 to 6 carbon atoms indicated by R$^2$ include methyl, ethyl, propyl, isopropyl, butyl, sec-butyl, tert-butyl, pentyl and hexyl groups.

As specific examples, the compound having a phosphorylcholine group may be a diamine compound in which X$^1$ and X$^2$ in the formula (I) are both amino groups, or a dicarboxylic acid compound in which X$^1$ and X$^2$ in the formula (I) are both —COOR$^1$ groups.

When X$^1$ and X$^2$ in the formula (I) are both —COOR$^1$ groups, that is, when the compound having a phosphorylcholine group is a dicarboxylic acid compound, two R$^1$'s may be the same or different from each other and are each a hydrogen atom or a carboxyl-protective group. Of these, in the invention, it is preferred that two R$^1$'s are both hydrogen atoms or both carboxyl-protective groups.

When two R$^1$'s are both carboxyl-protective groups, they may be the same or different from each other and are each a group selected from: alkyl groups having 1 to 6 carbon atoms such as methyl, ethyl, isopropyl, butyl, pentyl and hexyl groups; substituted or unsubstituted arylmethyl groups such as benzyl, p-methylbenzyl, m-ethylbenzyl, p-methoxybenzyl, p-nitrobenzyl, m-chlorobenzyl, 1,4-dimethoxybenzyl, benzhydryl, di-(p-methoxyphenyl)methyl and trityl groups; cyclic ether residues such as tetrahydropyranyl, tetrahydrofuranyl and 1,4-dioxane-2-yl groups; and alkylsilyl or alkylphenylsilyl groups such as trimethylsilyl, tert-butyldimethylsilyl and tert-butyldiphenylsilyl groups.

Further, the compound having a phosphorylcholine group preferably has the following formula (I-A):

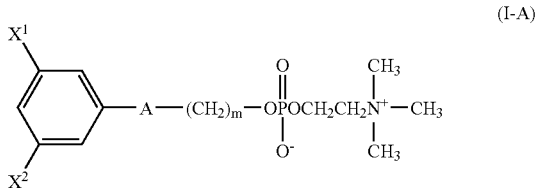

(I-A)

wherein $X^1$, $X^2$, A and m are as defined in the formula (I).

<<Production of the Diamine Compound>>

The compound having a phosphorylcholine group of the formula (I) in which $X^1$ and $X^2$ are both amino groups, that is, the diamine compound (hereinafter "diamine compound of the invention") may be produced by the following method.

A dinitro compound having a hydroxyl group represented by the formula (III):

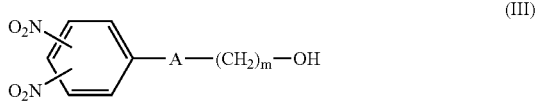

(III)

is reacted with 2-chloro-2-oxo-1,3,2-dioxaphosphorane (hereinafter "COP") to synthesize a dinitro compound having a phosphoryl group represented by the formula (IV):

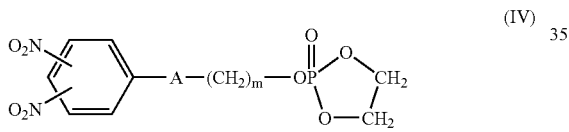

(IV)

Subsequently, the dinitro compound (IV) is reacted with trimethylamine to afford a dinitro compound having a phosphorylcholine group represented by the formula (V):

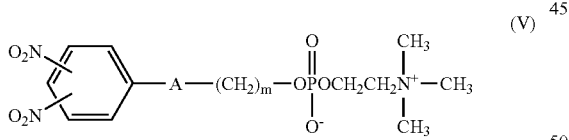

(V)

Thereafter, the nitro groups in the compound (V) are reduced to produce the compound having a phosphorylcholine group of the formula (I) in which $X^1$ and $X^2$ are both amino groups, namely the diamine compound of the invention.

In the above formula (III) to (V), A and m are as defined in the formula (I).

The dinitro compound having a hydroxyl group represented by the formula (III) may be easily synthesized from commercially available compounds using known reaction methods, as described in Examples 1 and 4 presented later.

The reaction between the dinitro compound of the formula (III) and COP is preferably performed such that they are used in a molar ratio of 1:1 to 1:5 (dinitro compound (III):COP) and such that the reaction is carried out in the presence of a tertiary amine compound such as triethylamine to capture hydrogen chloride generated or while blowing an inert gas into the reaction system to expel the hydrogen chloride.

In the subsequent ring-opening addition reaction between the dinitro compound of the formula (IV) and trimethylamine (hereinafter "TMA"), they are preferably used in a molar ratio of 1:1 to 1:5 (dinitro compound (IV):TMA).

The reduction of the nitro groups which follows may take place easily by reaction with a typical reducing agent, such as diborane, lithium borohydride, sodium borohydride, sodium aluminum hydride, sodium dialkoxyaluminum hydride or sodium diethylaluminum hydride. The reaction may proceed more favorably in the presence of a catalyst such as tin chloride. It is also possible to carry out catalytic reduction reaction in a hydrogen atmosphere under catalysis by a metal such as nickel, platinum, palladium or rhodium.

The above reactions are preferably carried out at atmospheric pressure or under pressure in an appropriate solvent. The solvent used herein may be any type that takes no part in the reaction, and examples thereof include methanol, ethanol, tetrahydrofuran, dimethoxyethane, dioxane, benzene and toluene. The reaction temperature is in the range of −100 to 150° C., and preferably −50 to 100° C.

<<Production of the Dicarboxylic Acid Compound>>

The compound having a phosphorylcholine group of the formula (I) in which $X^1$ and $X^2$ are both —$COOR^1$ groups, that is, the dicarboxylic acid compound (hereinafter "dicarboxylic acid compound of the invention") may be produced by the following method.

A dicarboxylic acid compound having a hydroxyl group represented by the formula (VI):

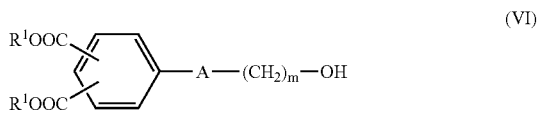

(VI)

is reacted with COP to synthesize a dicarboxylic acid compound having a phosphoryl group represented by the formula (VII):

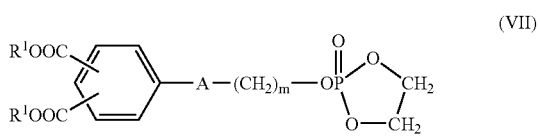

(VII)

Subsequently, the compound (VII) is reacted with TMA to afford the dicarboxylic acid compound of the invention.

In the above formula (VI) and (VII), $R^1$'s may be the same or different from each other and are each a hydrogen atom or a carboxyl-protective group, and A and m are as defined in the formula (I).

The dicarboxylic acid compound having a hydroxyl group represented by the formula (VI) may be easily synthesized from commercially available compounds using known reaction methods, as described in Examples 2 and 3 presented later.

Further, details such as molar ratio of the reactants and reaction conditions in the reaction of the compound (VI) with COP and the ring-opening addition reaction of the compound (VII) with TMA, are as described in the production of the diamine compound.

The compound of the formula (I) wherein $X^1$ and $X^2$ are both —$COOR^1$ groups and $R^1$'s are both hydrogen atoms, that is, the dicarboxylic acid compound of the invention having two carboxyl groups, may be obtained as follows: The compound of the formula (I) in which $X^1$ and $X^2$ are both —$COOR^1$ groups and $R^1$'s are carboxyl-protective groups, namely, the dicarboxylic acid compound of the formula (I-B) illustrated below is synthesized by the aforesaid method, and the protective groups $R^3$ of the dicarboxylic acid compound (I-B) are substituted with hydrogen atoms by appropriate reaction of removing the protective groups:

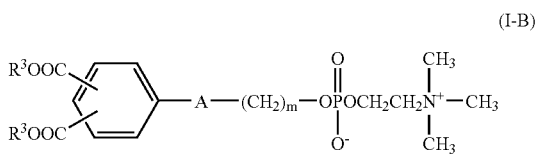

(I-B)

wherein each $R^3$ is a carboxyl-protective group, and A and m are as defined in the formula (I).

The carboxyl-protective groups $R^1$ and $R^3$ in the formula (I), (I-B), (VI) and (VII) are appropriately selected so that they will be stable in the above reaction processes and can be eliminated in the reaction of removing the protective groups without any damage to the other sites.

The preferred carboxyl-protective groups that satisfy these requirements include the alkyl groups having 1 to 6 carbon atoms, the substituted or unsubstituted arylmethyl groups, the cyclic ether residues, the alkylsilyl groups and the alkylphenylsilyl groups mentioned hereinabove.

The carboxyl-protective groups may be introduced into a corresponding precursor compound according to a known method (for example, see T. W. Greene, P. G. M. Wuts, "Protective Groups in Organic Synthesis, Third Edition", John Wiley & Sons, New York, 1999, pp. 372-431).

The reaction of removing the protective groups may be carried out by established methods depending on the type of the protective groups (for example, see T. W. Greene, P. G. M. Wuts, "Protective Groups in Organic Synthesis, Third Edition", John Wiley & Sons, New York, 1999, pp. 372-431).

<Polymer and Production Process Thereof>

<<Polymer Having a Phosphorylcholine Side Group>>

The polymer according to the present invention comprises at least 1 mol % of repeating units having a phosphorylcholine group and has a number-average molecular weight of 1,000 or more. The repeating units are represented by the formula (II):

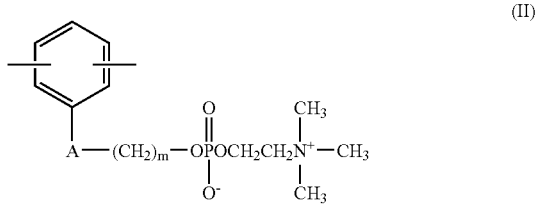

(II)

wherein A and m are as defined in the formula (I).

Herein, the term "polymer" is used in a broad sense to refer to homopolymer and copolymer. The copolymer may be a random copolymer, a block copolymer or a graft copolymer.

The polymer's number-average molecular weight is generally 1,000 or more, preferably 5,000 or more, and more preferably from 10,000 to 500,000. This range of molecular weight is desirable because the polymer having a molecular weight within the range exhibits superior mechanical strength, heat resistance and stability. The number-average molecular weight is measured and the value is shown in terms of polystyrene by gel permeation chromatography.

To exhibit biocompatibility, it is preferably required that the polymer contains at least 1 mol % of the repeating units with a phosphorylcholine group represented by the formula (II). Where the intended use requires higher biocompatibility, the repeating units are desirably contained at 5 mol % or more, and more preferably at 5 to 50 mol %. The content of the repeating units with a phosphorylcholine group represented by the formula (II) in the polymer may be easily controlled by manipulating the feeding ratio of the monomer, i.e., the compound having a phosphorylcholine group, in polymerization process described later.

The repeating units having a phosphorylcholine group are preferably represented by the following formula (II-A):

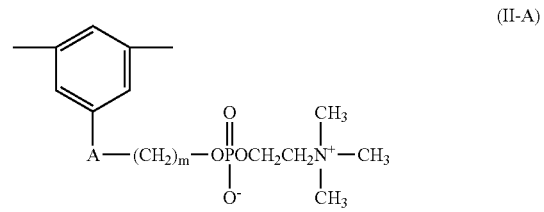

(II-A)

wherein A and m are as defined in the formula (I).

The polymer preferably has one or more bonds selected from an amido bond, an ester bond, a urethane bond, a urea bond and an imido bond within its main chain skeleton.

<<Production Process of the Polymer>>

The polymer of the invention may be produced by polycondensation or polyaddition of the compound having a phosphorylcholine group of the formula (I) as a starting raw monomer with another polymerizable monomer. As used herein, the term "another polymerizable monomer" refers to a monomer that is other than and is polymerizable with the compound having a phosphorylcholine group represented by the formula (I).

The polymerizable monomers include a dicarboxylic acid, a dicarboxylic acid derivative, a tetracarboxylic dianhydride, a diisocyanate compound, a diamine compound and a diol compound. Preferably, one or more of these monomers are used.

When the diamine compound of the invention is subjected to the polycondensation or polyaddition reaction with the polymerizable monomer which is a dicarboxylic acid and/or a dicarboxylic acid derivative, a polyamide having an amide bond in its main chain skeleton results. The reaction with a tetracarboxylic dianhydride to form a polyamide acid and subsequent imidation by chemical or heat treatment afford a polyimide having an imide bond in its main chain skeleton. The use of a diisocyanate compound leads to a polyurea having a urea bond in its main chain skeleton.

In the polycondensation or polyaddition reaction, the diamine compound of the invention is preferably used as a mixture with a different kind of diamine compound conventionally known. This combined use is preferable in view of that the resultant polymer exhibits higher mechanical strength and heat resistance. The known diamine compounds include those of the formula (XVII) described later. When the additional diamine compound is used, the diamine compound in relation to the invention is mixed therewith so as to achieve 1 mol % or more, preferably 5 mol % or more, and more preferably from 5 to 50 mol % relative to all the diamine compounds combined. This concentration is desirable in view of development of biocompatibility of the resultant polymer.

It is also possible to enhance the polymer's mechanical strength and heat resistance by other means. For example, a diisocyanate compound and a diol compound may be polymerized and the resulting polymer may be combined with the diamine compound of the invention to produce a poly (urethane-urea) having a urethane bond and a urea bond in its main chain skeleton.

The dicarboxylic acids and dicarboxylic acid derivatives employable as the polymerizable monomers include compounds represented by the formula (XI):

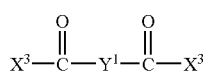

(XI)

wherein $Y^1$ is a divalent organic group, and $X^3$'s are each a hydroxyl group, a halogen atom or an alkoxy group. Accordingly, the repeating units of the polyamide obtained in this case, that is, the repeating units which contain the structural units of the formula (II) of the polymer according to the invention are represented by the formula (XII):

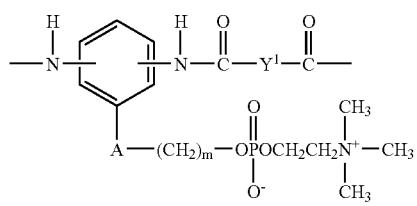

(XII)

wherein $Y^1$ is a divalent organic group, and A and m are as defined in the formula (I).

Specific examples of the dicarboxylic acids represented by the formula (XI) include phthalic acid, terephthalic acid, isophthalic acid, 2,6-naphthalenedicarboxylic acid, 1,6-naphthalenedicarboxylic acid, 2,6-anthracenedicarboxylic acid, 1,6-anthracenedicarboxylic acid, 4,4'-biphenyldicarboxylic acid, 4,4'-diphenylmethanedicarboxylic acid, 4,4'-diphenyletherdicarboxylic acid, 2,2'-bis(4-carboxylphenyl) propane, 2,2'-bis(4-carboxyphenoxyphenyl)propane, oxalic acid, fumaric acid, maleic acid, malonic acid, succinic acid, glutaric acid, adipic acid, pimelic acid, suberic acid, azelaic acid, sebacic acid, 1,9-nonanedicarboxylic acid and 1,10-decanedicarboxylic acid. Examples of the dicarboxylic acid derivatives include acid halides and alkyl esters of the above dicarboxylic acids. They may be used singly or in combination of two or more kinds.

The tetracarboxylic dianhydrides employable as the polymerizable monomers include compounds represented by the formula (XIII):

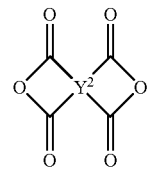

(XIII)

wherein $Y^2$ is a tetravalent organic group. Accordingly, the repeating units of the polyimide obtained in this case, that is, the repeating units which contain the structural units of the formula (II) of the polymer according to the invention are represented by the formula (XIV):

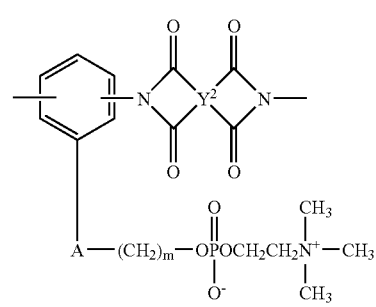

(XIV)

wherein $Y^2$ is a tetravalent organic group, and A and m are as defined in the formula (I).

Specific examples of the tetracarboxylic dianhydrides represented by the formula (XIII) include pyromellitic dianhydride, 2,3,6,7-naphthalenetetracarboxylic dianhydride, 1,2,5,6-naphthalenetetracarboxylic dianhydride, 1,4,5,8-naphthalenetetracarboxylic dianhydride, 2,3,6,7-anthracenetetracarboxylic dianhydride, 1,2,5,6-anthracenetetracarboxylic dianhydride, 3,3',4,4'-diphenyltetracarboxylic dianhydride, bis(3,4-dicarboxyphenyl)ether dianhydride, 3,3',4,4'-benzophenonetetracarboxylic dianhydride, bis(3,4-dicarboxyphenyl)sulfone dianhydride, bis(3,4-dicarboxyphenyl)methane dianhydride, 2,2-bis(3,4-dicarboxyphenyl)propane dianhydride, 1,1,1,3,3,3-hexafluoro-2,2-bis(3,4-dicarboxyphenyl)propane dianhydride, bis(3,4-dicarboxyphenyl)dimethylsilane dianhydride, bis(3,4-dicarboxyphenyl)diphenylsilane dianhydride, 2,3,5,6-pyridinetetracarboxylic dianhydride, 2,6-bis(3,4-dicarboxyphenoxy)pyridine dianhydride, cyclobutanetetracarboxylic dianhydride, cyclopentanetetracarboxylic dianhydride, cyclohexanetetracarboxylic dianhydride and 3,4-dicarboxy-1,2,3,4-tetrahydro-1-naphthalene-succinic tetracarboxylic dianhydride. They may be used singly or in combination of two or more kinds.

The diisocyanate compounds employable as the polymerizable monomers include compounds represented by the formula (XV):

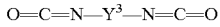

(XV)

wherein $Y^3$ is a divalent organic group. Accordingly, the repeating units of the polyurea obtained in this case, that is, the repeating units which contain the structural units of the formula (II) of the polymer according to the invention are represented by the formula (XVI):

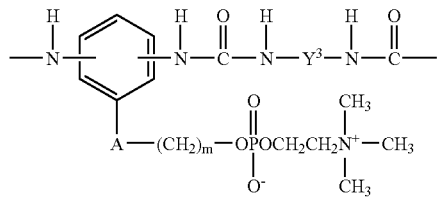

wherein $Y^3$ is a divalent organic group, and A and m are as defined in the formula (I).

Specific examples of the diisocyanate compounds represented by the formula (XV) include 1,4-phenylene diisocyanate, 1,3-phenylene diisocyanate, 1,4-xylylene diisocyanate, 1,3-xylylene diisocyanate, 2,4-toluylene diisocyanate, 2,5-toluylene diisocyanate, 4,4'-biphenylene diisocyanate, 4,4'-diphenylether diisocyanate, 4,4'-diphenylmethane diisocyanate, 4,4'-(2,2-diphenylpropane) diisocyanate, tetramethylene diisocyanate, pentamethylene diisocyanate, hexamethylene diisocyanate, heptamethylene diisocyanate and octamethylene diisocyanate. They may be used singly or in combination of two or more kinds.

Meanwhile, when the dicarboxylic acid compound of the invention is subjected to the polycondensation or polyaddition with the polymerizable monomer which is a diamine compound, a polyamide having an amide bond in its main chain skeleton results. The use of a diol compound leads to a polyester having an ester bond in its main chain skeleton.

In the polycondensation or polyaddition, the dicarboxylic acid compound of the invention is preferably used as a mixture with a different kind of dicarboxylic acid compound conventionally known. This combined use is preferable in view of that the resultant polymer exhibits higher mechanical strength and heat resistance. The known dicarboxylic acid compounds include the aforesaid dicarboxylic acids and dicarboxylic acid derivatives of the formula (XI). When the additional dicarboxylic acid compound is used, the dicarboxylic acid compound of the invention is mixed therewith so as to achieve 1 mol % or more, preferably 5 mol % or more, and more preferably from 5 to 50 mol % relative to all the dicarboxylic acid compounds combined. This content range is desirable in view of development of biocompatibility of the resultant polymer.

It is also possible to enhance the polymer's mechanical strength and heat resistance by other means. For example, a diisocyanate compound and a diol compound may be polymerized and the resulting polymer may be combined with the dicarboxylic acid compound of the invention to produce a poly(urethane-ester) having a urethane bond and an ester bond in its main chain skeleton.

The diamine compounds employable as the polymerizable monomers include compounds represented by the formula (XVII):

$$H_2N—Y^4—NH_2 \qquad (XVII)$$

wherein $Y^4$ is a divalent organic group. Accordingly, the repeating units of the polyamide obtained in this case, that is, the repeating units which contain the structural units of the formula (II) of the polymer according to the invention are represented by the formula (XVIII):

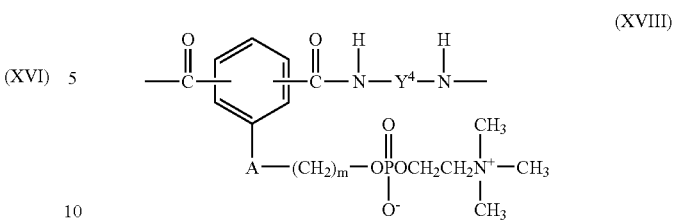

wherein $Y^4$ is a divalent organic group, and A and m are as defined in the formula (I).

Specific examples of the diamine compounds represented by the formula (XVII) include 1,4-phenylenediamine, 1,3-phenylenediamine, 2,5-diaminotoluene, 2,6-diaminotoluene, 4,4'-diaminobiphenyl, 3,3'-dimethyl-4,4'-diaminobiphenyl, 3,3'-dimethoxy-4-4'-diaminobiphenyl, 4,4'-diaminodiphenylmethane, 4,4'-diamino-3,3'-dimethyldiphenylmethane, 4,4'-diaminodiphenylether, 2,2'-bis(4-aminophenyl)propane, 4,4'-diaminodiphenylsulfone, 4,4'-diaminobenzophenone, 1,4-bis(4-aminophenyl)benzene, 1,4-bis(4-aminophenoxy)benzene, 4,4'-bis(4-aminophenoxy)diphenylsulfone, 2,2'-bis[4-(4-aminophenoxy)phenyl]propane, bis(4-aminocyclohexyl)methane, piperazine, 2-methylpiperazine, ethylenediamine, 1,3-diaminopropane, tetramethylenediamine, pentamethylenediamine, hexamethylenediamine, heptamethylenediamine, octamethylenediamine, nonamethylenediamine, decamethylenediamine, dodecamethylenediamine, 3,5-diaminobenzyloxypropylpentamethyldisiloxane, α,ω-bis(aminopropyl)polydimethylsiloxane and polydimethylsiloxane having a diamino group at its one end. (For synthesis methods of the above compounds, see Nagase et al., Makromoleculare Chemistry, Rapid communication, vol. 11, pp. 185-191, 1990; Akiyama et al., Makromoleculare Chemistry, vol. 193, pp. 1509-1519, 1992; and Nagase et al., Transactions of the Material Research Society of Japan, vol. 28, pp. 1259-1262, 2003.) They may be used singly or in combination of two or more kinds.

The diol compounds employable as the polymerizable monomers include compounds represented by the formula (XIX):

$$HO—Y^5—OH \qquad (XIX)$$

wherein $Y^5$ is a divalent organic group. Accordingly, the repeating units of the polyester obtained in this case, that is, the repeating units which contain the structural units of the formula (II) of the polymer according to the invention are represented by the formula (XX):

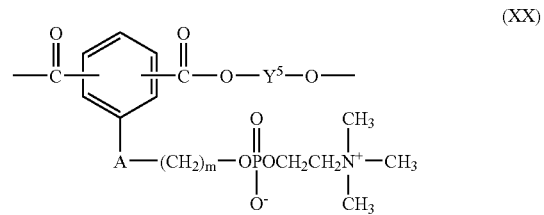

wherein $Y^5$ is a divalent organic group, and A and m are as defined in the formula (I).

Specific examples of the diol compounds represented by the formula (XIX) include hydroquinone, 1,3-phenylene diol, 1,4-xylylene diol, 1,3-xylylene diol, 2,4-toluylene diol, 2,5-toluylene diol, 4,4'-biphenylene diol, 4,4'-diphenylether diol, 4,4'-diphenylmethane diol, bisphenol A, ethylene glycol, propylene glycol, tetramethylene glycol, pentamethylene glycol, hexamethylene glycol, heptamethylene glycol, octamethylene glycol, polyethylene glycol and polypropylene glycol. They may be used singly or in combination of two or more kinds.

To carry out the polycondensation or polyaddition reaction of the compound having a phosphorylcholine group of the formula (I) and the other polymerizable monomer, any literature methods may be employed (e.g., "Macromolecular Synthesis" edited by J. A. Moore, John Wiley & Sons, New York, 1997, "Polymer Syntheses" edited by S. R. Sandler and W. Karo, Academic Press, Inc., Boston, 1992, and "New Polymer Experiments" edited by The Society of Polymer Science, Japan, vol. 3, Polymer Synthesis Reactions (2)—Syntheses of Condensation Polymers, Kyoritsu Shuppan Co., Ltd., 1996).

EFFECTS OF THE INVENTION

By using the compound having a phosphorylcholine group of the invention, a novel polymer having a phosphorylcholine side group may be easily synthesized. The polymer of the invention exhibits excellent processability and superior heat resistance, hydrolysis resistance, mechanical strength and biocompatibility. Accordingly, the polymer may be used as materials for manufacturing artificial organs such as artificial blood vessels and other various medical devices that have excellent heat resistance, hydrolysis resistance, mechanical strength and biocompatibility.

EXAMPLES

The present invention will be hereinafter described in further detail through Examples and Comparative Examples presented below, but it should be construed that the invention is in no way limited to those Examples.

In Examples and Comparative Examples, the molecular weight was measured under the following conditions:

Chromatograph: Gel Permeation Chromatography HLC-802A (manufactured by TOSOH CORPORATION)

Solvent: dimethylformamide (1.0 ml/min)

Columns: four TSK GEL columns (G5000H6, G4000H6, G3000H6 and G2000H6 manufactured by TOSOH CORPORATION)

Measurement temperature: 40° C.

Standard: polystyrene

Example 1

Synthesis 1 of a Diamine Compound of the Invention

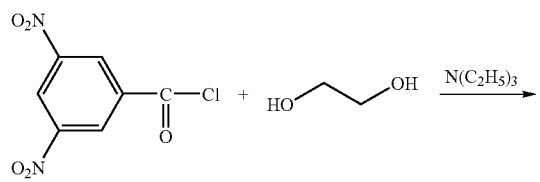

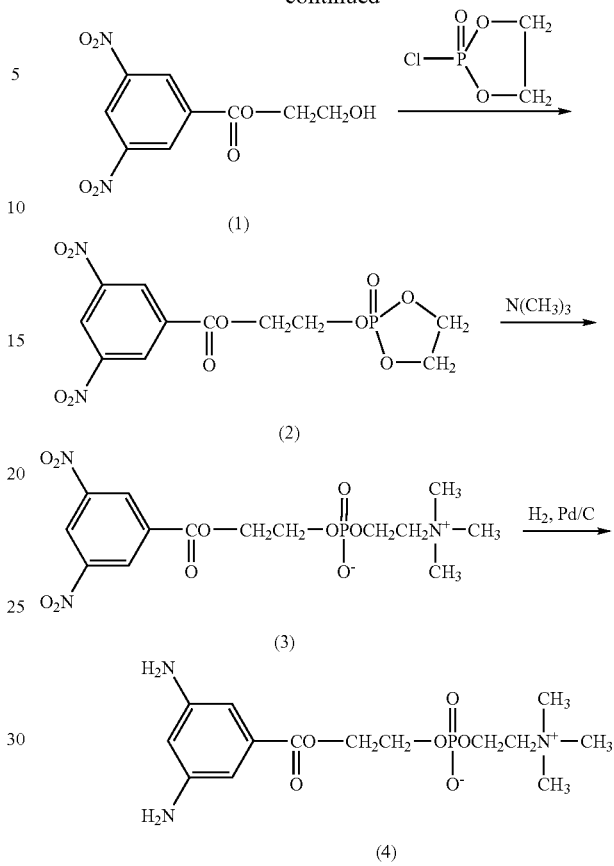

<Synthesis of Compound (1)>

In an argon atmosphere, ethylene glycol (24.0 ml, 430 mmol), dry tetrahydrofuran (340 ml) and dry triethylamine (60.0 ml) were mixed in a three-necked flask to give a solution. To the solution was slowly added dropwise a solution of 3,5-dinitrobenzoyl chloride (10.0 g, 43.4 mmol) in dry tetrahydrofuran (150 ml), with the flask in an ice water bath. After the completion of the dropwise addition, the mixture was stirred for 20 hours at room temperature. Subsequently, the product was extracted with chloroform and washed with distilled water. The organic liquid phase was dehydrated with sodium sulfate and then filtered off, and the solvent was distilled away under reduced pressure. Thereafter, purification of the residue was performed by silica gel column chromatography (developing solvent: hexane/ethyl acetate=1:1 (by volume)) to obtain an alcoholic compound represented by the above formula (1) as a yellow solid (amount: 8.95 g, yield: 80.6%). The compound structure was identified by the $^1$H-NMR and IR spectra given below:

$^1$H-NMR, δ(400 MHz, CDCl$_3$, ppm): 1.92 (1H, t, J=5.61 Hz), 3.98 (2H, m), 4.54 (2H, m), 9.13 (2H, d, J=2.20 Hz), 9.18 (1H, t, J=2.20 Hz).

IR, ν(KBr neat, cm$^{-1}$): 3222, 3045, 2879, 1722, 1627, 1595, 1541, 1344, 1172, 1078, 844, 723, 528.

<Synthesis of Compound (2)>

In an argon atmosphere, the above-prepared compound (1) (8.00 g, 31.2 mmol), dry tetrahydrofuran (150 ml) and dry triethylamine (8.80 ml) were mixed in a three-necked flask. With the flask in an ice water bath and the contents being stirred, 2-chloro-2-oxo-1,3,2-dioxaphosphorane (5.60 ml, 62.4 mmol) was slowly added dropwise. After the completion of the dropwise addition, the mixture was stirred for 2 hours at room temperature. Subsequently, the precipitate was filtered with suction, dissolved in chloroform and washed with distilled water. The organic liquid phase was dehydrated with sodium sulfate and then filtered off, and the solvent was distilled away under reduced pressure to give a phosphorane compound represented by the above formula (2) as a white solid (amount: 5.28 g, yield: 46.7%). The compound structure was identified by the $^1$H-NMR and IR spectra given below:

$^1$H-NMR, δ(400 MHz, CDCl$_3$, ppm): 4.41-4.58 (6H, m), 4.69 (2H, m), 9.24 (1H, t, J=2.20 Hz), 9.28 (2H, d, J=2.20 Hz). IR, ν(KBr neat, cm$^{-1}$): 3107, 2974, 1720, 1587, 1550, 1360, 1290, 1164, 1060, 931, 721, 611.

<Synthesis of Compound (3)>

In an argon atmosphere, the above-prepared compound (2) (4.05 g, 11.2 mmol) was dissolved in dry acetonitrile (60.0 ml) in an eggplant-shaped flask. The solution was then combined with trimethylamine (1.01 ml, 11.2 mmol) in a −30° C. coolant bath. The flask was then sealed, and reaction was carried out overnight at 60° C. Subsequently, the reaction liquid was concentrated by distilling away the solvent under reduced pressure. Cooling in a coolant bath caused precipitation. The precipitate was filtered with suction in a stream of argon to give a dinitro compound having a phosphorylcholine group represented by the above formula (3) as a light yellow solid (amount: 4.59 g, yield: 97.4%). The compound structure was identified by the $^1$H-NMR and IR spectra given below:

$^1$H-NMR, δ(400 MHz, DMSO-d$_6$, ppm): 3.13 (9H, s), 3.51 (2H, m), 4.02 (2H, m), 4.06 (2H, m), 4.51 (2H, t, J=4.64 Hz), 8.96 (2H, d, J=2.20 Hz), 9.06 (1H, t, J=2.20 Hz). IR, ν(KBr neat, cm$^{-1}$): 3400, 2493, 2250, 2135, 1732, 1633, 1537, 1454, 1353, 1172, 856, 773, 731.

<Synthesis of Compound (4)>

The above-prepared compound (3) (4.50 g, 10.71 mmol) was dissolved in ethanol (60.0 ml) in an eggplant-shaped flask. The solution was then combined with 5% palladium-containing carbon powder (0.45 g, 0.18 mmol), and the mixture was cooled to about −80° C. in an aceton-dry ice bath. After the flask had been purged with hydrogen, reaction was carried out overnight at room temperature. Subsequently, the reaction solution was combined with 100 ml of tetrahydrofuran, and the mixture was filtered through Celite. The filtrate was distilled under reduced pressure to remove the solvent, thereby obtaining a diamine compound having a phosphorylcholine group represented by the above formula (4) as a yellow solid (amount: 4.30 g, yield: 92.1%). The compound structure was identified by the $^1$H-NMR and IR spectra given below:

$^1$H-NMR, δ(400 MHz, DMSO-d$_6$, ppm): 3.15 (9H, s), 3.53 (2H, m), 4.00 (2H, m), 4.10 (2H, m), 4.43 (2H, t, J=4.64 Hz), 7.77 (1H, s), 7.81 (1H, s), 8.03 (1H, s), 8.98 (2H, s), 9.13 (2H, s). IR, ν(KBr neat, cm$^{-1}$): 3199, 2885, 1718, 1535, 1477, 1228, 1076, 966, 733.

Example 2

Synthesis 1 of a Dicarboxylic Acid Compound of the Invention

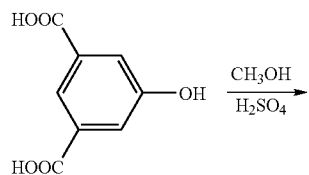

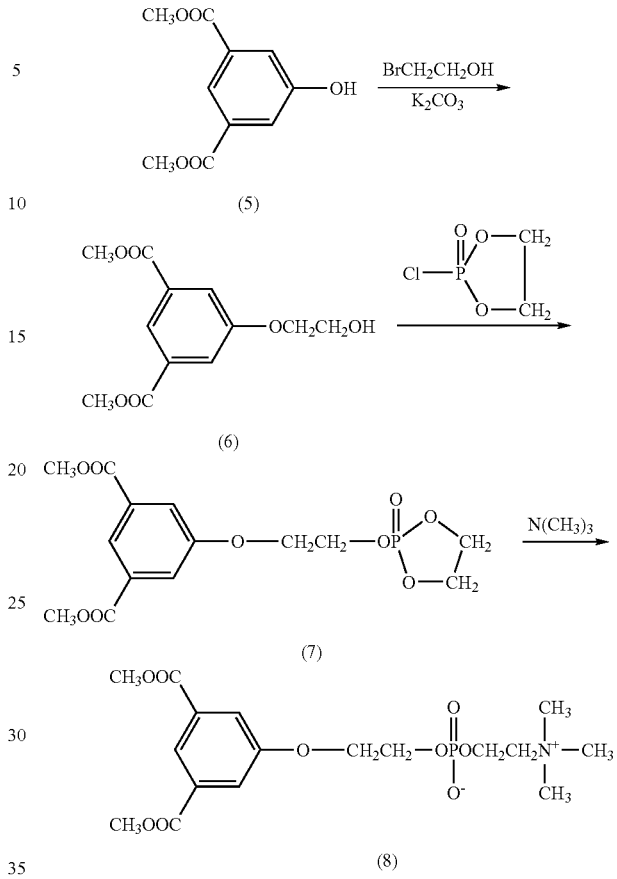

<Synthesis of Compound (5)>

5-Hydroxyisophthalic acid (16.2 g, 89.0 mmol) was dispersed in 150 ml of methanol in an eggplant-shaped flask. The dispersion was combined with 3.0 ml of concentrated sulfuric acid, and the mixture was refluxed at 75° C. for 3 hours and half. After the reaction, distilled water and a saturated aqueous solution of sodium hydrogencarbonate were added in excess. The precipitate formed was filtered off and dried under reduced pressure. The resultant solid was purified by recrystallization method using a hexane/chloroform mixed solvent to afford methyl 5-hydroxyisophthalate represented by the above formula (5) as a white solid (amount: 13.8 g, yield: 73.8%). The compound structure was identified by the $^1$H-NMR spectrum given below:

$^1$H-NMR, δ(400 MHz, CDCl$_3$, ppm): 3.87 (6H, s), 6.25 (1H, s), 7.64 (2H, d, J=1.47 Hz), 8.17 (1H, t, J=1.46 Hz).

<Synthesis of Compound (6)>

The above-prepared compound (5) (12.0 g, 57.0 mmol), dimethylsulfoxide (70 ml), potassium carbonate (10.4 g, 84.0 mmol) and 2-bromoethanol (6.08 ml, 85.6 mmol) were mixed in an eggplant-shaped flask. The mixture was then stirred at 100° C. for 5 hours. Subsequently, the reaction liquid was cooled to room temperature and poured into excess ice water. The resultant precipitate was extracted with chloroform and washed with distilled water. The organic liquid phase was dehydrated with sodium sulfate and then filtered off, and the solvent was distilled away under reduced pressure. Thereafter, purification of the residue was performed by silica gel column chromatography (developing solvent: hexane/ethyl acetate=2:1 (by volume)) to obtain an alcoholic compound represented by the above formula (6) as a white solid (amount: 6.56 g, yield: 54.2%). The compound structure was identified by the ¹H-NMR spectrum given below:

¹H-NMR, δ(400 MHz, CDCl₃, ppm): 3.92 (6H, s), 3.98 (2H, t, J=4.15 Hz), 4.16 (2H, t, J=4.55 Hz), 4.50 (1H, d, J=1.22 Hz), 7.76 (2H, t, J=0.73 Hz), 8.23 (1H, t, J=1.47 Hz).

<Synthesis of Compound (7)>

In an argon atmosphere, the above-prepared compound (6) (3.00 g, 11.8 mmol), dry tetrahydrofuran (60 ml) and dry triethylamine (3.40 ml) were mixed in a three-necked flask. With the flask in an ice water bath and the contents being stirred, 2-chloro-2-oxo-1,3,2-dioxaphosphorane (2.12 ml, 23.6 mmol) was slowly added dropwise. After the completion of the dropwise addition, the mixture was stirred for 2 hours at room temperature. Subsequently, the precipitate was filtered with suction, dissolved in chloroform and thereafter washed with distilled water. The organic liquid phase was dehydrated with sodium sulfate and then filtered off, and the solvent was distilled away under reduced pressure to give a phosphorane compound represented by the above formula (7) as a white solid (amount: 2.00 g, yield: 46.7%). The compound structure was identified by the ¹H-NMR spectrum given below:

¹H-NMR, δ(400 MHz, CDCl₃, ppm): 3.65 (2H, m), 3.95 (6H, s), 4.15-4.50 (6H, m), 7.79 (2H, d, J=1.25 Hz), 8.31 (1H, t, J=1.30 Hz).

<Synthesis of Compound (8)>

In an argon atmosphere, the above-prepared compound (7) (1.50 g, 4.16 mmol) was dissolved in dry acetonitrile (20.0 ml) in an eggplant-shaped flask. The solution was then combined with trimethylamine (0.50 ml, 5.47 mmol) in a −30° C. coolant bath. The flask was then sealed, and reaction was carried out overnight at 60° C. Subsequently, the reaction liquid was concentrated by distilling away the solvent under reduced pressure. Cooling in a coolant bath caused precipitation. The precipitate was filtered with suction in a stream of argon to give a dicarboxylate compound having a phosphorylcholine group represented by the above formula (8) as a white solid (amount: 1.70 g, yield: 97.4%). The compound structure was identified by the ¹H-NMR spectrum given below:

¹H-NMR, δ(400 MHz, CDCl₃, ppm): 3.46 (9H, s), 3.93 (6H, s), 4.13-4.26 (8H, m), 7.68 (2H, d, J=1.28 Hz), 8.23 (1H, t, J=1.30 Hz).

Example 3

Synthesis 2 of a Dicarboxylic Acid Compound of the Invention

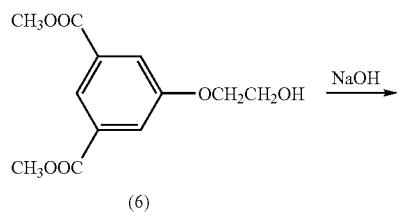

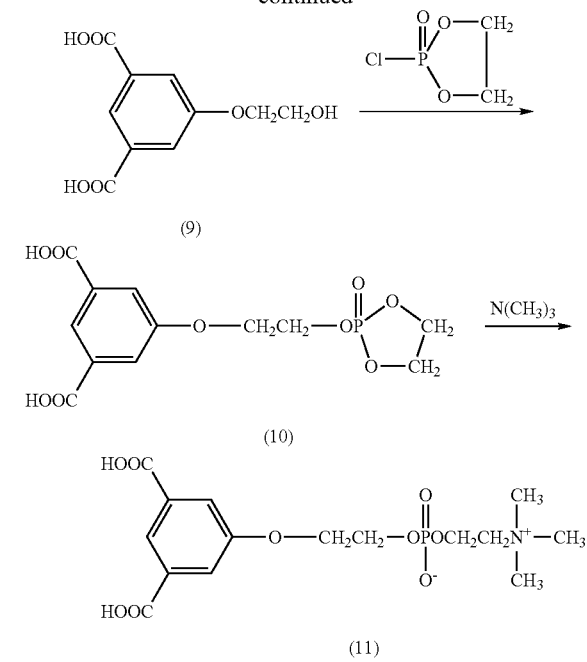

<Synthesis of Compound (9)>

The compound (6) (3.40 g, 15.8 mmol) prepared in Example 2 was dissolved in 64 ml of tetrahydrofuran. The solution was combined with 50 ml of an aqueous solution containing 3.74 g of sodium hydroxide, and the mixture was refluxed for 72 hours. Subsequently, the reaction liquid was cooled to room temperature and concentrated hydrochloric acid was added thereto to adjust the pH to approximately 1 to 2. After the tetrahydrofuran had been distilled away from the mixture under reduced pressure, excess distilled water was added and the mixture was allowed to stand. Thereafter, the precipitate formed was filtered off, and the solid obtained was purified by recrystallization method using a hexane-chloroform mixed solvent to afford an alcoholic compound represented by the above formula (9) as a white solid (amount: 2.43 g, yield: 68.1%). The compound structure was identified by the ¹H-NMR spectrum given below:

¹H-NMR, δ(400 MHz, DMSO-d₆, ppm): 4.31 (2H, m), 4.68 (2H, t, J=4.88 Hz), 5.51 (1H, m), 8.23 (2H, d, J=1.46 Hz), 8.65 (1H, t, J=1.34 Hz), 13.89 (2H, bs).

<Synthesis of Compound (10)>

In an argon atmosphere, the above-prepared compound (9) (2.00 g, 8.85 mmol), dry tetrahydrofuran (40 ml) and dry triethylamine (2.20 ml) were mixed in a three-necked flask. With the flask in an ice water bath and the contents being stirred, 2-chloro-2-oxo-1,3,2-dioxaphosphorane (1.50 ml, 16.7 mmol) was slowly added dropwise. After the completion of the dropwise addition, the mixture was stirred for 2 hours at room temperature. Subsequently, the precipitate was filtered with suction, dissolved in a chloroform-dimethylformamide mixed solvent and washed with distilled water. The organic liquid phase was dehydrated with sodium sulfate and then filtered off, and the solvent was distilled away under reduced pressure to give a phosphorane compound represented by the above formula (10) as a white solid (amount: 1.34 g, yield: 45.5%). The compound structure was identified by the ¹H-NMR spectrum given below:

$^1$H-NMR, δ(400 MHz, DMSO-d$_6$, ppm): 3.57 (2H, m), 4.20-4.50 (6H, m), 7.66 (2H, m), 8.08 (1H, m), 10.06 (2H, s).

<Synthesis of Compound (11)>

In an argon atmosphere, the above-prepared compound (10) (1.30 g, 3.91 mmol) was dissolved in dry acetonitrile (30.0 ml) in an eggplant-shaped flask. The solution was combined with trimethylamine (0.50 ml, 5.47 mmol) in a −30° C. coolant bath. The flask was then sealed, and reaction was carried out overnight at 60° C. Subsequently, the reaction liquid was concentrated by distilling away the solvent under reduced pressure. Cooling in a coolant bath caused precipitation. The precipitate was filtered with suction in a stream of argon to give a dicarboxylic acid compound having a phosphorylcholine group represented by the above formula (11) as a white solid (amount: 1.45 g, yield: 95.0%). The compound structure was identified by the $^1$H-NMR spectrum given below:

$^1$H-NMR, δ(400 MHz, DMSO-d$_6$, ppm): 3.35 (9H, s), 3.74 (2H, m), 4.11 (2H, m), 4.50 (2H, m), 4.67 (2H, m), 7.63 (2H, t, J=1.95 Hz), 8.07 (1H, t, J=1.94 Hz), 8.98 (2H, bs).

Example 4

Synthesis 2 of a Diamine Compound of the Invention

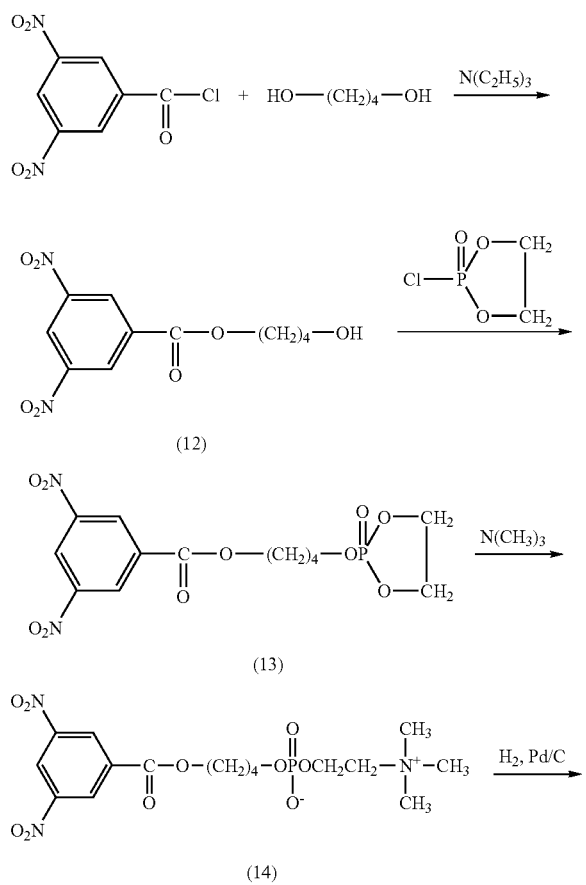

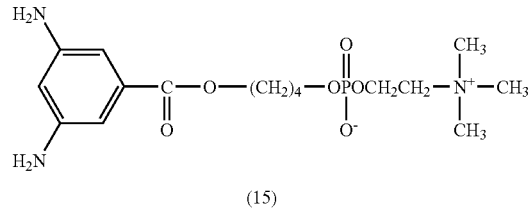

<Synthesis of Compound (12)>

In an argon atmosphere, 1,4-butanediol (38.3 ml, 434 mmol), dry tetrahydrofuran (340 ml) and dry triethylamine (60.0 ml) were mixed in a three-necked flask to give a solution. To the solution was slowly added dropwise a solution of 3,5-dinitrobenzoyl chloride (10.0 g, 43.4 mmol) and dry tetrahydrofuran (150 ml), with the flask in an ice water bath. After the completion of the dropwise addition, the mixture was stirred for 20 hours at room temperature. Subsequently, the product was extracted with chloroform and washed with distilled water. The organic liquid phase was dehydrated with sodium sulfate and then filtered off, and the solvent was distilled away under reduced pressure. Thereafter, purification of the residue was performed by silica gel column chromatography (developing solvent: hexane/ethyl acetate=1:1 (by volume)) to obtain an alcoholic compound represented by the above formula (12) as a yellow solid (amount: 9.74 g, yield: 79.0%). The compound structure was identified by the $^1$H-NMR and IR spectra given below:

$^1$H-NMR, δ(400 MHz, CDCl$_3$, ppm): 1.38 (1H, t, J=5.13 Hz), 1.75 (2H, m), 1.96 (2H, m), 3.76 (2H, m), 4.51 (2H, t, J=6.71 Hz), 9.17 (2H, d, J=1.95 Hz), 9.24 (1H, t, J=2.08 Hz).

IR, ν(KBr neat, cm$^{-1}$): 3250, 3105, 2961, 1728, 1628, 1541, 1462, 1348, 1281, 1169, 1072, 937, 777, 721.

<Synthesis of Compound (13)>

In an argon atmosphere, the above-prepared compound (12) (2.00 g, 7.04 mmol), dry tetrahydrofuran (15.0 ml) and dry triethylamine (4.00 ml) were mixed in a three-necked flask. With the flask in an ice water bath and the contents being stirred, 2-chloro-2-oxo-1,3,2-dioxaphosphorane (0.970 ml, 10.6 mmol) was slowly added dropwise. After the completion of the dropwise addition, the mixture was stirred for 2 hours at room temperature. Subsequently, the precipitate was filtered with suction, dissolved in chloroform and washed with distilled water. The organic liquid phase was dehydrated with sodium sulfate and then filtered off, and the solvent was distilled away under reduced pressure to give a phosphorane compound represented by the above formula (13) as a white solid (amount: 1.45 g, yield: 52.7%). The compound structure was identified by the $^1$H-NMR and IR spectra given below:

$^1$H-NMR, δ(400 MHz, CDCl$_3$, ppm): 1.88 (2H, m), 1.98 (2H, m), 4.26 (2H, m), 4.39 (2H, m), 4.47 (4H, m), 9.16 (2H, d, J=2.20 Hz), 9.24 (1H, t, J=2.08 Hz). IR, ν(KBr neat, cm$^{-1}$): 3108, 2964, 1715, 1628, 1553, 1470, 1352, 1290, 1180, 1109, 1047, 935, 833, 779, 584.

<Synthesis of Compound (14)>

In an argon atmosphere, the above-prepared compound (13) (7.22 g, 18.5 mmol) was dissolved in dry acetonitrile (100 ml) in an eggplant-shaped flask. The solution was combined with trimethylamine (3.44 ml, 37.0 mmol) in a −30° C. coolant bath. The flask was then sealed, and reaction was carried out overnight at 60° C. Subsequently, the reaction liquid was concentrated by distilling away the solvent under reduced pressure. Cooling in a coolant bath caused precipitation. The precipitate was filtered with suction in a stream of argon to give a dinitro compound having a phosphorylcholine group represented by the above formula (14) as a peach solid (amount: 8.26 g, yield: 99.3%). The compound structure was identified by the $^1$H-NMR and IR spectra given below:

$^1$H-NMR, δ(400 MHz, DMSO-$d_6$, ppm): 3.19 (9H, s), 3.58 (2H, m), 3.86 (2H, m), 4.13 (2H, m), 4.35-4.47 (6H, m), 8.97 (2H, d, J=2.56 Hz), 9.08 (1H, d, J=1.95 Hz). IR, ν(KBr neat, cm$^{-1}$): 3108, 2960, 1715, 1625, 1553, 1470, 1352, 1290, 1230, 1075, 1047, 853, 735.

<Synthesis of Compound (15)>

The above-prepared compound (14) (1.06 g, 2.36 mmol) was dissolved in ethanol (50.0 ml) in an eggplant-shaped flask. The solution was then combined with 5% palladium-containing carbon powder (0.10 g), and the mixture was cooled to about –80° C. in an aceton-dry ice bath. After the flask had been purged with hydrogen, reaction was carried out overnight at room temperature. Subsequently, the reaction solution was combined with 100 ml of tetrahydrofuran, and the mixture was filtered through Celite. The filtrate was distilled under reduced pressure to remove the solvent to give a diamine compound having a phosphorylcholine group represented by the above formula (15) as a yellow solid (amount: 0.850 g, yield: 92.5%). The compound structure was identified by the $^1$H-NMR and IR spectra given below:

$^1$H-NMR, δ(400 MHz, DMSO-$d_6$, ppm): 3.16 (9H, s), 3.58 (2H, m), 3.86 (2H, m), 4.39 (4H, m), 5.38 (4H, d, J=5.86 Hz), 7.79 (2H, d, J=25.4 Hz), 8.02 (1H, s), 11.67 (4H, s). IR, ν(KBr neat, cm$^{-1}$): 3200, 3108, 2960, 1718, 1625, 1553, 1470, 1352, 1290, 1230, 1075, 1047, 853, 733.

Example 5

Synthesis 1 of a Polyamide Copolymer

In an argon atmosphere, the compound (4) (0.37 g, 0.94 mmol) prepared in Example 1, 4,4'-diamino-3,3'-dimethyl-diphenylmethane (1.91 g, 8.45 mmol) and isophthalic acid chloride (1.91 g, 9.39 mmol) were mixed in an eggplant-shaped flask and cooled to about –80° C. in an aceton-dry ice bath. Subsequently, the mixture was combined with dry N-methylpyrrolidinone (33.8 ml), and the mixture was allowed to react for 6 hours while the temperature was slowly raised to ambient. After the reaction, the reaction solution was poured into excess ethanol to precipitate the polymer. The precipitated polymer was filtered off and dried under reduced pressure to give 2.02 g of a polyamide copolymer having a phosphorylcholine group represented by the above formula PA-1 as light brown powder. The copolymer structure was identified by the $^1$H-NMR spectrum given below:

$^1$H-NMR, δ(400 MHz, DMSO-$d_6$, ppm): 2.21 (s, —CH$_3$), 3.08 (S, N—CH$_3$), 3.55 (m, —CH$_2$—), 3.89 (s, —CH$_2$—), 4.17 (m, —CH$_2$—), 4.52 (m, —CH$_2$—), 7.08 (m, -Ph-), 7.15 (m, -Ph-), 7.28 (m, -Ph-), 7.65 (m, -Ph-), 8.13 (m, -Ph-), 8.27 (m, -Ph-), 8.53 (m, -Ph-), 8.72 (m, -Ph-), 8.87 (m, -Ph-), 9.98 (s, —NH—).

The composition ratio of x/y in PA-1 was determined to be 91/9 from the evaluation of the peak area ratio in the $^1$H-NMR spectrum. Gel permeation chromatography (solvent: dimethylformamide, standard: polystyrene) for PA-1 provided number-average molecular weight of 5.50×10$^3$ and weight-average molecular weight of 1.9×10$^4$. PA-1 showed a glass transition temperature (softening point) of about 215° C. as determined by differential scanning calorimetry, indicating sufficient heat resistance for medical device applications.

The copolymer PA-1 was found to be soluble in aprotic polar solvents such as N-methylpyrrolidinone, dimethylformamide and dimethylsulfoxide, and to be insoluble in water, methanol, ethanol, chloroform, acetone, tetrahydrofuran and

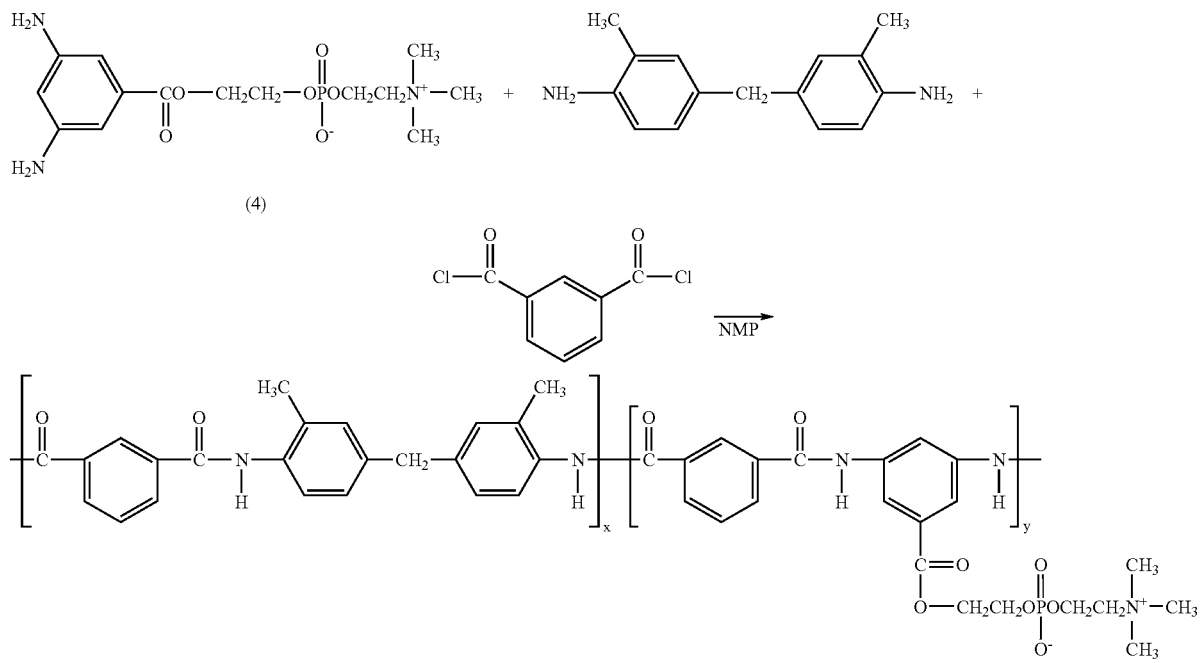

PA-1, PA-2, PA-3, PA-4 acrylonitrile. The PA-1's solubility in specific solvents works advantageously making of materials, such as coatings and hollow filaments. On the other hand, insolubility in many other solvents gives advantages that devices produced from the copolymer show superior durability.

A strong film was obtained from dimethylformamide solution of the copolymer PA-1 by a solvent cast method.

Example 6

Synthesis 2 of a Polyamide Copolymer

Polymerization and purification were carried out by the procedures illustrated in Example 5 using the compound (4) (0.12 g, 0.31 mmol) prepared in Example 1, 4,4'-diamino-3,3'-dimethyldiphenylmethane (0.21 g, 0.94 mmol), isophthalic acid chloride (0.25 g, 1.25 mmol) and dry N-methylpyrrolidinone (3.8 ml). As a result, 0.25 g of a polyamide copolymer (PA-2) having a phosphorylcholine group represented by the same formula as PA-1 was obtained as light brown powder. The $^1$H-NMR spectrum of PA-2 was similar to that of PA-1 shown in Example 5.

The composition ratio of x/y in PA-2 was determined to be 86/14 from the evaluation of the peak area ratio in the $^1$H-NMR spectrum. Gel permeation chromatography (solvent: dimethylformamide, standard: polystyrene) for PA-2 provided number-average molecular weight of $5.90\times10^3$ and weight-average molecular weight of $2.91\times10^4$. PA-2 showed a glass transition temperature (softening point) of about 180° C. as determined by differential scanning calorimetry. Also, PA-2 was found to have similar solubility characteristics to those of PA-1.

A strong film was obtained from dimethylformamide solution of the copolymer PA-2 by a solvent cast method.

Example 7

Synthesis 3 of a Polyamide Copolymer

Polymerization and purification were carried out by the procedures illustrated in Example 5 using the compound (4) (0.32 g, 0.89 mmol) prepared in Example 1, 4,4'-diamino-3,3'-dimethyldiphenylmethane (0.47 g, 2.07 mmol), isophthalic acid chloride (0.60 g, 2.96 mmol) and dry N-methylpyrrolidinone (5.9 ml). As a result, 1.02 g of a polyamide copolymer (PA-3) having a phosphorylcholine group represented by the same formula as PA-1 was obtained as light brown powder. The $^1$H-NMR spectrum of PA-3 was similar to that of PA-1 shown in Example 5.

The composition ratio of x/y in PA-3 was determined to be 80/20 from the evaluation of the peak area ratio in the $^1$H-NMR spectrum. Gel permeation chromatography (solvent: dimethylformamide, standard: polystyrene) for PA-3 provided number-average molecular weight of $4.11\times10^3$ and weight-average molecular weight of $6.19\times10^3$. PA-3 showed a glass transition temperature (softening point) of about 152° C. as determined by differential scanning calorimetry. Also, PA-3 was found to have similar solubility characteristics to those of PA-1.

A strong film was obtained from dimethylformamide solution of the copolymer PA-3 by a solvent cast method.

Example 8

Synthesis 4 of a Polyamide Copolymer

Polymerization and purification were carried out by the procedures illustrated in Example 5 using the compound (4) (0.28 g, 0.78 mmol) prepared in Example 1, 4,4'-diamino-3,3'-dimethyldiphenylmethane (0.26 g, 1.17 mmol), isophthalic acid chloride (0.40 g, 1.95 mmol) and dry N-methylpyrrolidinone (3.9 ml). As a result, 0.79 g of a polyamide copolymer having a phosphorylcholine group represented by the same formula as PA-1 was obtained as light brown powder. The $^1$H-NMR spectrum of PA-4 was similar to that of PA-1 shown in Example 5.

The composition ratio of x/y in PA-4 was determined to be 50/50 from the evaluation of the peak area ratio in the $^1$H-NMR spectrum. Gel permeation chromatography (solvent: dimethylformamide, standard: polystyrene) for PA-4 provided number-average molecular weight of $5.25\times10^3$ and weight-average molecular weight of $1.43\times10^4$. PA-4 showed a glass transition temperature (softening point) of about 150° C. as determined by differential scanning calorimetry. Also, PA-4 was found to have similar solubility characteristics to those of PA-1.

A strong film was obtained from dimethylformamide solution of the copolymer PA-4 by a solvent cast method.

Example 9

Synthesis 5 of a Polyamide Copolymer

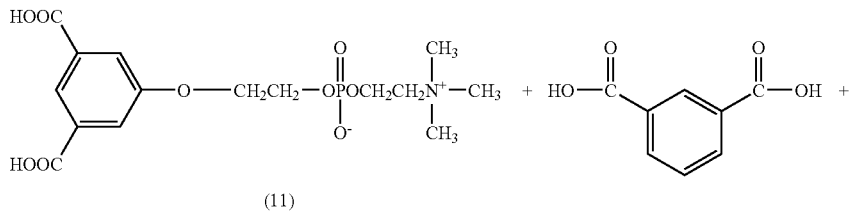

(11)

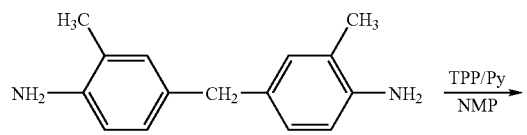

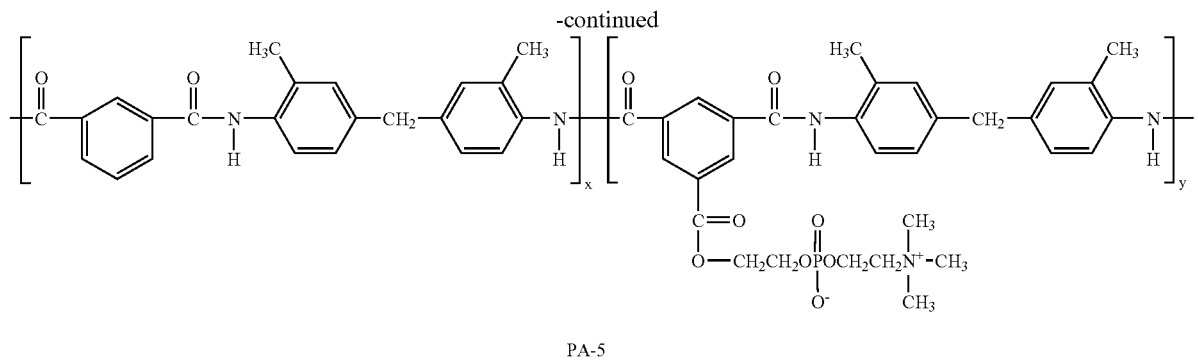

PA-5

In an argon atmosphere, the compound (11) (0.150 g, 0.384 mmol) prepared in Example 3, 4,4'-diamino-3,3'-dimethyldiphenylmethane (0.174 g, 0.768 mmol) and isophthalic acid (0.0637 g, 0.383 mmol) were mixed in an eggplant-shaped flask and dissolved by addition of dry N-methylpyrrolidinone (1.53 ml), pyridine (0.12 ml) and triphenyl phosphite (0.40 ml). The resultant solution was stirred at 80° C. for 24 hours. The reaction solution obtained was cooled to room temperature and poured into excess methanol to precipitate the obtained polymer. The precipitated polymer was filtered off and dried under reduced pressure to give 0.30 g of a polyamide copolymer having a phosphorylcholine group represented by the above formula PA-5 as light brown powder. The copolymer structure was identified by the $^1$H-NMR spectrum given below:

$^1$H-NMR, δ(400 MHz, DMSO-d$_6$, ppm): 2.13 (s, —CH$_3$), 3.12 (S, N—CH$_3$), 3.88 (m, —CH$_2$—), 4.09 (s, —CH$_2$—), 4.27 (m, —CH$_2$—), 4.47 (m, —CH$_2$—), 4.66 (m, —CH$_2$—), 6.90 (m, -Ph-), 7.01 (m, -Ph-), 7.10 (m, -Ph-), 7.25 (m, -Ph-), 7.68 (m, -Ph-), 8.08 (m, -Ph-), 8.48 (m, -Ph-), 8.52 (m, -Ph-), 9.10 (s, —NH—), 9.97 (s, —NH—).

The composition ratio of x/y in PA-5 was determined to be 78/22 from the evaluation of the peak area ratio in the $^1$H-NMR spectrum. Gel permeation chromatography (solvent: dimethylformamide, standard: polystyrene) for PA-5 provided number-average molecular weight of $1.04 \times 10^4$ and weight-average molecular weight of $3.91 \times 10^4$. PA-5 showed a glass transition temperature (softening point) of about 180° C. as determined by differential scanning calorimetry. Also, PA-5 was found to have similar solubility characteristics to those of PA-1.

A strong film was obtained from dimethylformamide solution of the copolymer PA-5 by a solvent cast method.

Example 10

Synthesis 6 of a Polyamide Copolymer

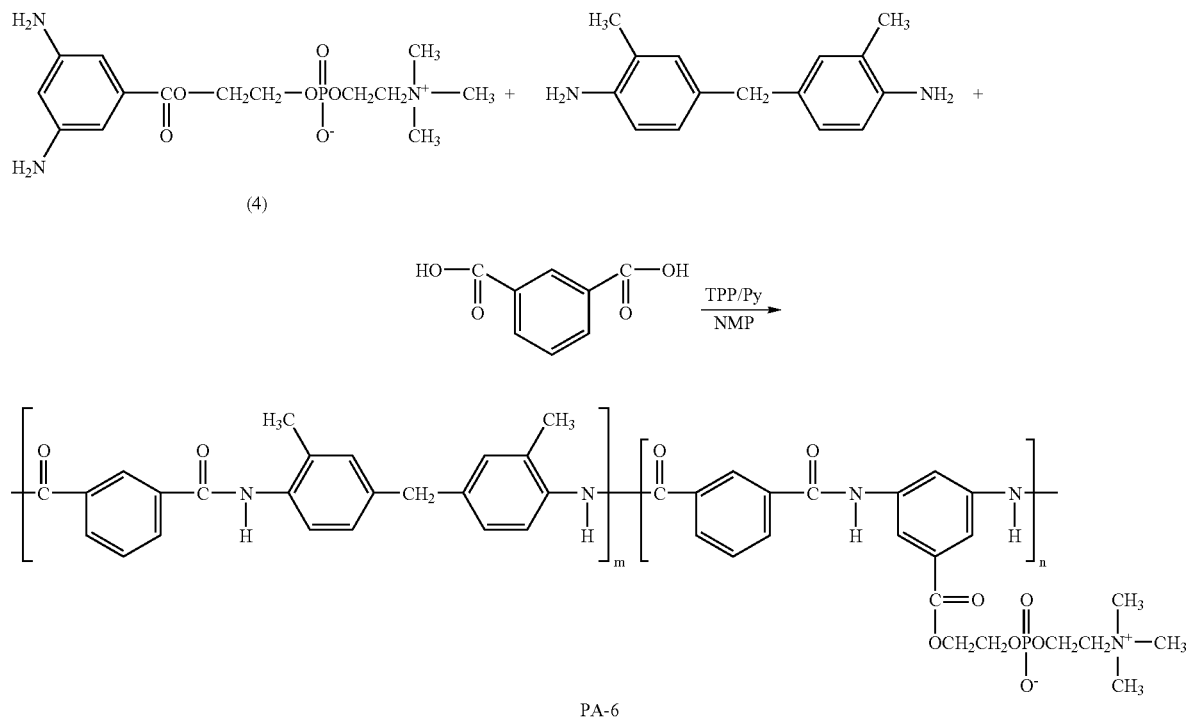

PA-6

In an argon atmosphere, the compound (4) (0.20 g, 0.55 mmol) prepared in Example 1, 4,4'-diamino-3,3'-dimethyl-diphenylmethane (1.12 g, 4.95 mmol) and isophthalic acid (0.91 g, 5.50 mmol) were mixed in an eggplant-shaped flask and dissolved by addition of dry N-methylpyrrolidinone (10.0 ml), pyridine (2.90 ml) and triphenyl phosphite (0.88 ml). The resultant solution was stirred at 100° C. for 24 hours. The reaction solution obtained was cooled to room temperature and poured into excess methanol to precipitate the obtained polymer. The precipitated polymer was filtered off and dried under reduced pressure to give 1.77 g of a polyamide copolymer having a phosphorylcholine group represented by the above formula PA-6 as light brown powder. The copolymer structure was identified by the $^1$H-NMR spectrum given below:

$^1$H-NMR, δ(400 MHz, DMSO-$d_6$, ppm): 2.13 (s, —CH$_3$), 3.12 (s, N—CH$_3$), 3.88 (m, —CH$_2$—), 4.09 (s, —CH$_2$—), 4.27 (m, —CH$_2$—), 4.47 (m, —CH$_2$—), 4.66 (m, —CH$_2$—), 6.90 (m, -Ph-), 7.01 (m, -Ph-), 7.10 (m, -Ph-), 7.25 (m, -Ph-), 7.68 (m, -Ph-), 8.08 (m, -Ph-), 8.48 (m, -Ph-), 8.52 (m, -Ph-), 9.10 (s, —NH—), 9.97 (s, —NH—).

The composition ratio of m/n in PA-6 was determined to be 98/2 from the evaluation of the peak area ratio in the $^1$H-NMR spectrum. Gel permeation chromatography (solvent: dimethylformamide, standard: polystyrene) for PA-6 provided number-average molecular weight of $1.52 \times 10^4$ and weight-average molecular weight of $6.48 \times 10^4$. PA-6 showed a glass transition temperature (softening point) of about 205° C. as determined by differential scanning calorimetry. Also, PA-6 was found to have similar solubility characteristics to those of PA-1.

A strong film was obtained from dimethylformamide solution of the copolymer PA-6 by a solvent cast method.

Example 11

Synthesis 7 of a Polyamide Copolymer

In an argon atmosphere, the compound (4) (0.10 g, 0.28 mmol) prepared in Example 1, 2,2'-bis(4-aminophenoxy phenyl)propane (1.02 g, 2.49 mmol) and 2,2'-bis(4-carboxyphenoxy phenyl)propane (1.30 g, 2.77 mmol) were mixed in an eggplant-shaped flask and dissolved by addition of dry N-methylpyrrolidinone (5.00 ml), pyridine (0.44 ml) and triphenyl phosphite (1.50. ml). The resultant solution was stirred at 100° C. for 24 hours. The reaction solution obtained was cooled to room temperature and poured into excess methanol to precipitate the obtained polymer. The precipitated polymer was filtered off and dried under reduced pressure to give 2.24 g of a polyamide copolymer having a phosphorylcholine group represented by the above formula PA-7 as light brown powder. The copolymer structure was identified by the $^1$H-NMR spectrum given below:

$^1$H-NMR, δ(400 MHz, DMSO-$d_6$, ppm): 1.19 (s, —CH$_3$), 1.62 (s, —CH$_3$), 1.67 (s, —CH$_3$), 3.12 (s, N—CH$_3$), 4.12 (m, —CH$_2$—), 4.30 (m, —CH$_2$—), 4.47 (m, —CH$_2$—), 4.66 (m, —CH$_2$—), 6.74 (m, -Ph-), 6.88 (m, -Ph-), 7.00 (m, -Ph-), 7.07 (m, -Ph-), 7.11 (m, -Ph-), 7.21 (m, -Ph-), 7.30 (m, -Ph-), 7.75 (m, -Ph-), 7.88 (m, -Ph-), 7.97 (m, -Ph-), 9.28 (s, —NH—), 10.2 (s, —NH—).

The composition ratio of m/n in PA-7 was determined to be 95/5 from the evaluation of the peak area ratio in the $^1$H-NMR spectrum. Gel permeation chromatography (solvent: dimethylformamide, standard: polystyrene) for PA-7 provided number-average molecular weight of $1.44 \times 10^4$ and weight-average molecular weight of $3.39 \times 10^4$. PA-7 showed a glass transition temperature (softening point) of about 175° C. as determined by differential scanning calorimetry. Also, PA-7 was found to have similar solubility characteristics to those of PA-1.

A strong film was obtained from dimethylformamide solution of the copolymer PA-7 by a solvent cast method.

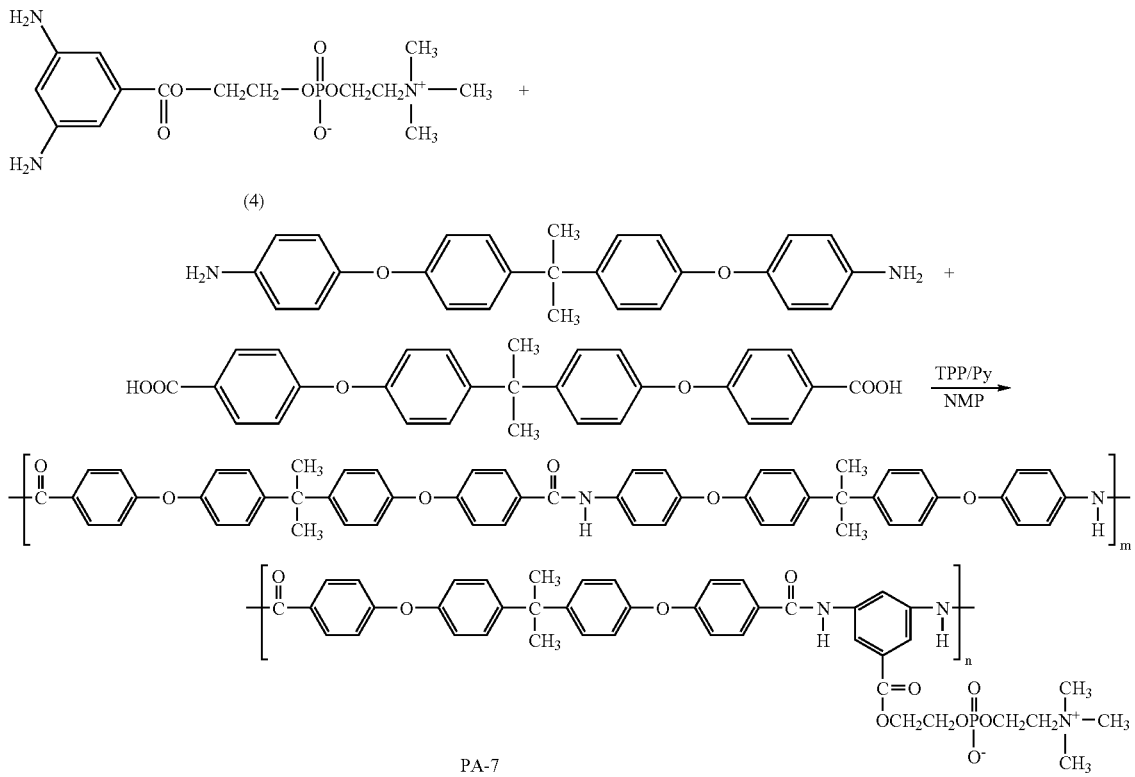

PA-7

Example 12

Synthesis 8 of a Polyamide Copolymer

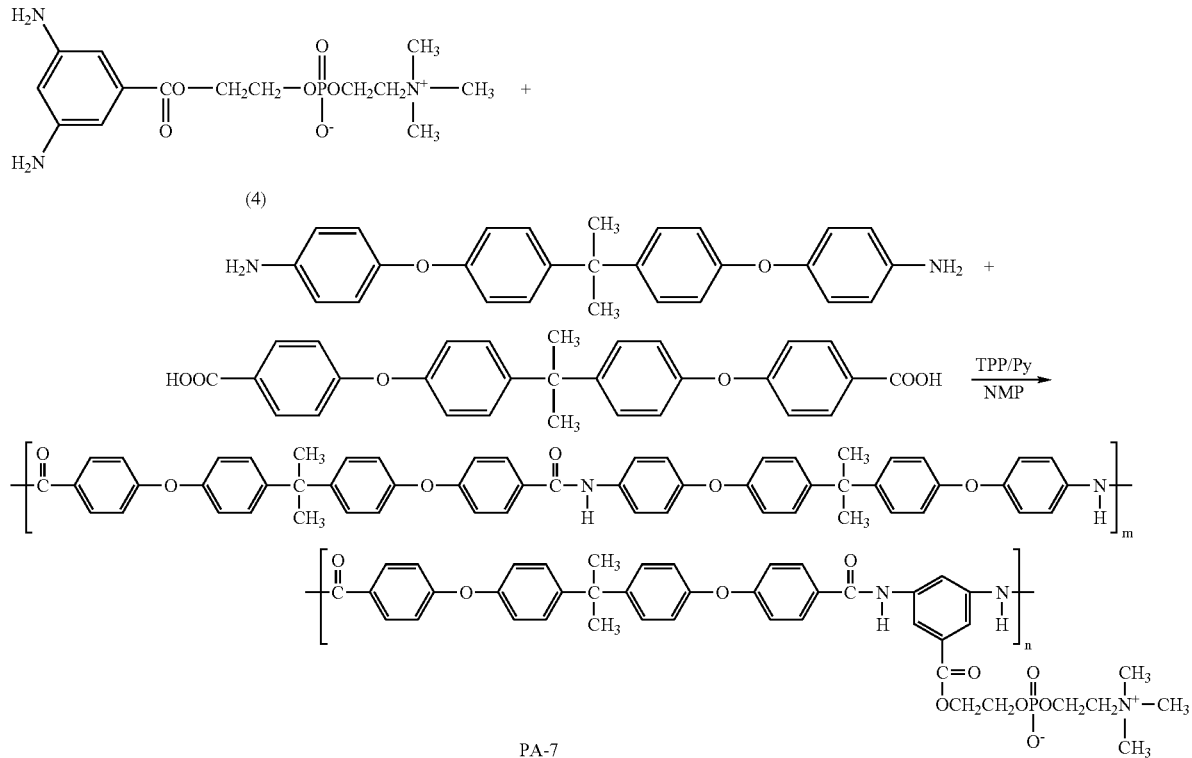

PA-7

In an argon atmosphere, the compound (4) (0.22 g, 0.63 mmol) prepared in Example 1, 3,5-diaminobenzyloxypropylpentamethyldisiloxane (1.00 g, 3.14 mmol) and 2,2'-bis(4-carboxyphenoxyphenyl)propane (1.77 g, 3.77 mmol) were mixed in an eggplant-shaped flask and dissolved by addition of dry N-methylpyrrolidinone (7.50 ml), pyridine (0.67 ml) and triphenyl phosphite (2.25 ml). The resultant solution was stirred at 100° C. for 24 hours. The reaction solution obtained was cooled to room temperature and poured into excess methanol to precipitate the obtained polymer. The precipitated polymer was filtered off and dried under reduced pressure to give 2.24 g of a polyamide copolymer having a phosphorylcholine group represented by the above formula PA-8 as light brown powder. The copolymer structure was identified by the $^1$H-NMR spectrum given below:

$^1$H-NMR, δ(400 MHz, DMSO-$d_6$, ppm): 0.00 (m, Si—$CH_3$), 0.21 (s, Si—$CH_3$), 0.49 (m, —$CH_3$—), 1.68 (s, —$CH_3$), 2.72 (m, —$CH_2$—), 3.15 (s, N—$CH_3$), 4.12 (m, —$CH_2$—) 4.43 (m, —$CH_2$—), 5.32 (m, —$CH_3$—), 6.77 (m, -Ph-), 7.08 (m, -Ph-), 7.18 (m, -Ph-), 7.33 (m, -Ph-), 7.46 (m, -Ph-), 7.89 (m, -Ph-), 8.01 (m, -Ph-), 8.22 (m, -Ph-), 9.35 (s, —NH—), 10.2 (s, —NH—).

The composition ratio of m/n in PA-8 was determined to be 85/15 from the evaluation of the peak area ratio in the $^1$H-NMR spectrum. Gel permeation chromatography (solvent: dimethylformamide, standard: polystyrene) for PA-8 provided number-average molecular weight of $2.17 \times 10^4$ and weight-average molecular weight of $2.93 \times 10^4$. PA-8 showed a glass transition temperature (softening point) of about 150° C. as determined by differential scanning calorimetry. Also, PA-8 was found to have similar solubility characteristics to those of PA-1.

A strong film was obtained from dimethylformamide solution of the copolymer PA-8 by a solvent cast method.

Example 13

Synthesis 1 of a Poly(Urethane-urea)

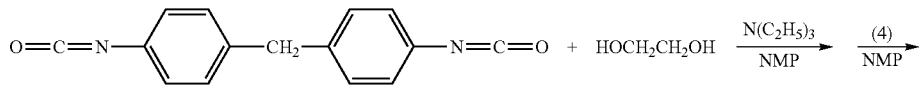

-continued

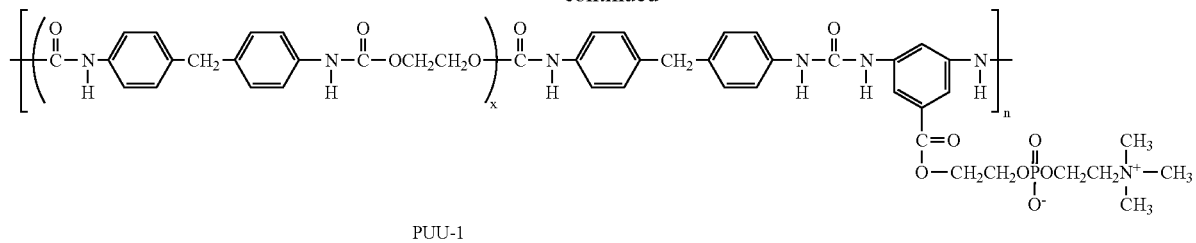

PUU-1

In an argon atmosphere, ethylene glycol (0.28 ml, 4.95 mmol) and triethylamine (0.5 ml) were dissolved in dry N-methylpyrrolidinone (5.0 ml) in a three-necked flask to give a solution. At room temperature, a solution of 4,4′-diphenylmethane diisocyanate (1.37 g, 5.50 mmol) in dry N-methylpyrrolidinone (5.0 ml) was slowly added dropwise to the solution. After the completion of the dropwise addition, the resultant solution was stirred for 1 hour at room temperature and was combined with a solution of the compound (4) (0.20 g, 0.55 mmol) prepared in Example 1 in dry N-methylpyrrolidinone (3.0 ml). The resultant mixture solution was stirred for 2 hours at room temperature. After the reaction, the reaction solution was poured into excess ethanol to precipitate the obtained polymer. The precipitated polymer was filtered off and dried under reduced pressure to give 1.34 g of a poly(urethane-urea) having a phosphorylcholine group represented by the above formula PUU-1 as light brown powder. The structure was identified by the $^1$H-NMR spectrum given below:

$^1$H-NMR, δ(400 MHz, DMSO-$d_6$, ppm): 2.95 (s, N—$CH_3$), 3.60 (m, —$CH_2$—), 3.73 (s, —$CH_2$—), 4.01 (m, —$CH_2$—), 4.29 (s, —$CH_2O$—), 6.73 (m, -Ph-), 7.08 (m, -Ph-), 7.13 (m, -Ph-), 7.32 (m, -Ph-), 7.43 (m, -Ph-), 7.88 (m, -Ph-), 9.30 (s, —NH—), 9.62 (s, —NH—).

The polyurethane segment in PUU-1 had an average polymerization degree x of about 9 as determined from the peak area ratio in the $^1$H-NMR spectrum. Gel permeation chromatography (solvent: dimethylformamide, standard: polystyrene) for PUU-1 provided number-average molecular weight of $3.60 \times 10^4$ and weight-average molecular weight of $1.50 \times 10^5$. The glass transition temperature (softening point) of PUU-1 was not observed in a temperature range of ambient to 300° C. by differential scanning calorimetry; therefore it is assumed to be higher than 300° C. This indicates that PUU-1 has sufficiently high heat resistance for medical device applications.

Also, PUU-1 was found to be soluble in aprotic polar solvents such as N-methylpyrrolidinone, dimethylformamide and dimethylsulfoxide, and to be insoluble in water, methanol, ethanol, chloroform, acetone, tetrahydrofuran and acrylonitrile. The PUU-1's solubility in specific solvents works advantageously making of materials, such as coatings and hollow filaments. On the other hand, insolubility in many other solvents gives advantages that devices produced from the copolymer show superior durability.

A strong film was obtained from dimethylformamide solution of the copolymer PUU-1 by a solvent cast method.

Example 14

Synthesis 2 of a Poly(Urethane-urea)

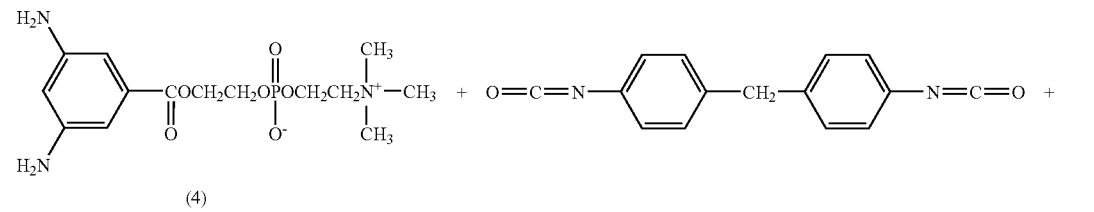

(4)

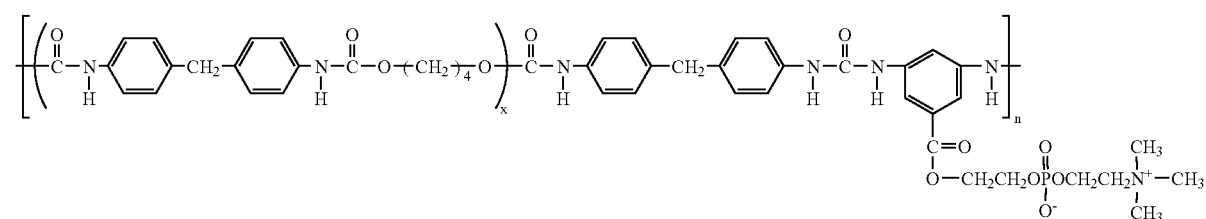

PUU-2

In an argon atmosphere, 1,4-butanediol (0.30 ml, 3.32 mmol) and triethylamine (0.2 ml) were dissolved in dry N-methylpyrrolidinone (5.0 ml) in a three-necked flask to give a solution. At room temperature, a solution of 4,4'-diphenylmethane diisocyanate (1.04 g, 4.15 mmol) in dry N-methylpyrrolidinone (10 ml) was slowly added dropwise to the solution. After the completion of the dropwise addition, the solution mixture was stirred for 1 hour at room temperature. Subsequently, a solution of the compound (4) (0.30 g, 0.83 mmol) prepared in Example 1 in dry N-methylpyrrolidinone (5.0 ml) was slowly added dropwise to the solution, followed by stirring for 2 hours at room temperature. After the reaction, the reaction solution was poured into excess methanol to precipitate the obtained polymer. The precipitated polymer was filtered off and dried under reduced pressure to give 2.20 g of a polyurethane represented by the above formula PUU-2 as white powder. The structure was identified by the $^1$H-NMR spectrum given below:

$^1$H-NMR, δ(400 MHz, DMSO-$d_6$, ppm): 1.72 (m, —$CH_2$—), 2.09 (s, —$CH_2$—), 3.14 (s, N—$CH_3$), 3.45 (m, —$CH_2$—), 3.78 (m, —$CH_2$—), 4.11 (m, —$CH_2$—), 4.42 (m, —$CH_2$—), 4.93 (m, —$CH_2$—), 5.28 (m, —$CH_2$—), 6.63 (m, -Ph-), 6.92 (m, -Ph-), 7.09 (m, -Ph-), 7.35 (m, -Ph-), 8.49 (s, —NH—), 9.48 (s, —NH—).

PUU-2 had a phosphorylcholine unit content of 5 mol % as determined from the peak area ratio in the $^1$H-NMR spectrum. Gel permeation chromatography (solvent: dimethylformamide, standard: polystyrene) for PUU-2 provided number-average molecular weight of $1.06 \times 10^4$ and weight-average molecular weight of $1.71 \times 10^4$. The glass transition temperature (softening point) of PUU-2 was not observed in a temperature range of ambient to 300° C. by differential scanning calorimetry. Also, PUU-2 was found to have similar solubility characteristics to those of PUU-1.

A strong film was obtained from dimethylformamide solution of the copolymer PUU-2 by a solvent cast method.

Example 15

Synthesis 3 of a Poly(Urethane-urea)

In an argon atmosphere, ethylene glycol (0.44 ml, 7.99 mmol), 4,4'-diphenylmethane diisocyanate (2.62 g, 9.59 mmol) and dibutyltin dilaurate (0.2 ml) were dissolved in dry N-methylpyrrolidinone (16 ml) in a three-necked flask to give a solution, followed by stirring for 2.5 hours at 50° C. Thereafter, a solution of polyethylene glycol (molecular weight: 1000, 0.80 g, 0.799 mmol) in dry N-methylpyrrolidinone (8 ml) was slowly added dropwise to the reaction solution at 50° C. After the completion of the dropwise addition, the solution was stirred for 1 hour at 50° C. Subsequently, a solution of the compound (4) (0.30 g, 0.799 mmol) prepared in Example 1 in dry N-methylpyrrolidinone (3 ml) was slowly added dropwise to the solution, followed by stirring for 18 hours at 50° C. After the reaction, the reaction solution was poured into excess methanol to precipitate the obtained polymer. The precipitated polymer was filtered off and dried under reduced pressure to give 3.25 g of a polyurethane represented by the above formula PUU-3 as white powder. The structure was identified by the $^1$H-NMR spectrum given below:

$^1$H-NMR, δ(400 MHz, DMSO-$d_6$, ppm): 3.30 (s, N—$CH_3$), 3.60 (m, —$CH_2$—), 3.79 (s, —$CH_2$—), 4.12 (m, —$CH_2$—), 4.30 (s, —$CH_2$—), 4.95 (m, —$CH_2$—), 6.61 (m, -Ph-), 6.90 (m, -Ph-), 7.06 (d, -Ph-), 7.35 (d, -Ph-), 9.60 (bs, —NH—).

PUU-3 had a phosphorylcholine unit content of 7.3 mol % as determined from the peak area ratio in the $^1$H-NMR spectrum. Gel permeation chromatography (solvent: dimethylformamide, standard: polystyrene) for PUU-3 provided number-average molecular weight of $3.66 \times 10^4$ and weight-average molecular weight of $7.61 \times 10^4$. The glass transition temperature (softening point) of PUU-3 was not observed in a temperature range of ambient to 200° C. by differential scanning calorimetry. Also, PUU-3 was found to have similar solubility characteristics to those of PUU-1.

A strong film was obtained from dimethylformamide solution of the copolymer PUU-3 by a solvent cast method.

Test Example

Blood-contact Test for Polymer Membranes

The polymers PA-1, PA-2, PA-3, PA-4, PA-5, PA-6, PA-7, PA-8, PUU-1, PUU-2 and PUU-3 produced in Examples 5

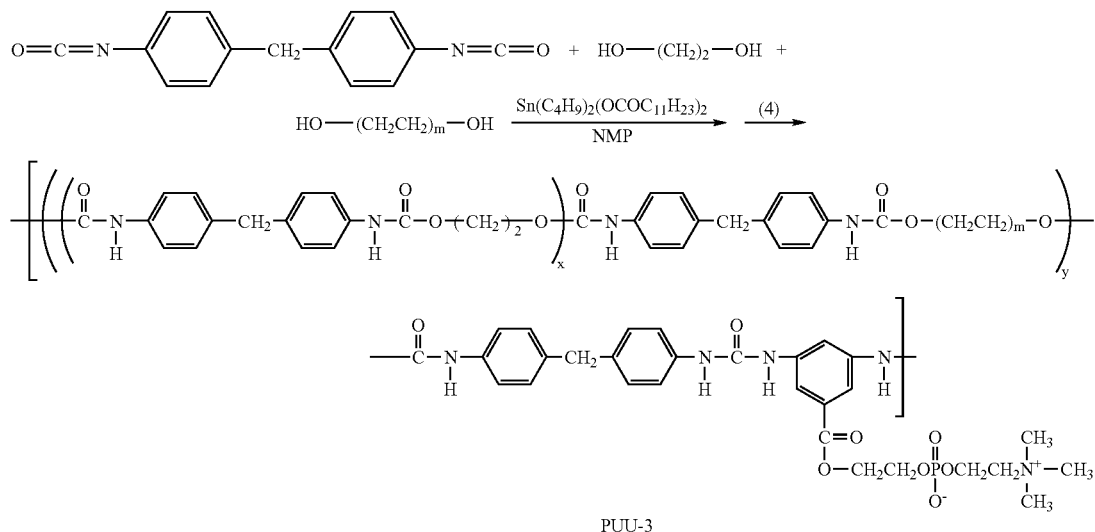

PUU-3 to 15 were each dissolved in dimethylformamide to achieve 1.5 wt % concentration. Polyethyleneterephthalate (PET) substrates (14 mm diameter, 0.2 mm thickness) were immersed in each of the above-formed solutions (5 ml) over a period of 2 hours at room temperature, so that polymer membranes were formed on the PET substrate surfaces. Subsequently, the PET substrates coated with the polymer membranes were each immersed in 2 ml of a phosphate buffer solution (pH=7.4) over a period of 24 hours at room temperature. After the phosphate buffer solution had been drawn out, the substrates were each immersed in 2 ml of human platelet rich plasma (PRP) from human blood over a period of 3 hours at 37° C. The polymer membrane surfaces subjected to the blood-contact test were washed three times with a phosphate buffer solution (pH=7.4). Subsequently, they were subjected to immobilization in an aqueous glutaraldehyde solution (2.5 wt %), washed three times with distilled water and freeze dried.

Thereafter, gold was deposited on the polymer membrane surfaces treated as described above, and the surfaces were observed with a scanning electron microscope. The results are shown in FIGS. 1 to 11.

As is clear from the figures, adsorption of platelets and proteins was scarcely observed on any of the polymer membrane surfaces. That is, these polymers had excellent antithrombotic properties, namely, blood compatibility.

Comparative Example 1

Synthesis of a Polyamide Having no Phosphorylcholine Group and Blood-contact Test

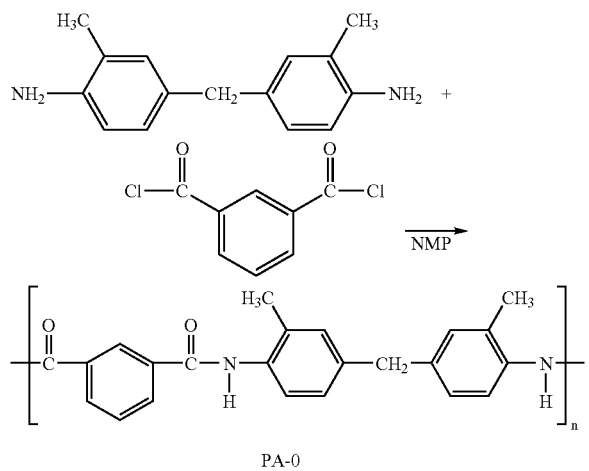

PA-0

<Synthesis of Polyamide>

In an argon atmosphere, 4,4'-diamino-3,3'-dimethyldiphenylmethane (1.00 g, 4.42 mmol) and isophthalic acid chloride (0.901 g, 4.42 mmol) were mixed in an eggplant-shaped flask and cooled to about −80° C. in an aceton-dry ice bath. Subsequently, the mixture was combined with dry N-methylpyrrolidinone (8.9 ml), and the newly formed mixture was allowed to react for 4 hours while the temperature was slowly raised to ambient. After the reaction, the reaction solution was poured into excess ethanol to precipitate the obtained polymer. The precipitated polymer was filtered off and dried under reduced pressure to give 1.54 g of a polyamide represented by the above formula PA-0 as white powder. The structure was identified by the $^1$H-NMR spectrum given below:

$^1$H-NMR, δ(400 MHz, DMSO-$d_6$, ppm): 2.21 (6H, s, —$CH_3$), 3.90 (2H, s, —$CH_2$—), 7.08 (2H, d, J=1.95 Hz, -Ph-), 7.13 (2H, s, -Ph-), 7.28 (2H, d, J=1.95 Hz, -Ph-), 7.63 (1H, t, J=7.08 Hz), 8.14 (2H, d, J=7.08 Hz), 8.55 (1H, s, -Ph-), 9.96 (2H, s, —NH—).

Gel permeation chromatography (solvent: dimethylformamide, standard: polystyrene) for PA-0 provided number-average molecular weight of $1.02 \times 10^4$ and weight-average molecular weight of $3.12 \times 10^4$. PA-0 showed a glass transition temperature (softening point) of about 190° C. as determined by differential scanning calorimetry. Also, PA-0 was found to have similar solubility characteristics to those of PA-1.

<Blood-contact Test>

The polymer PA-0 was dissolved in dimethylformamide to achieve 1.5 wt % concentration. A polyethyleneterephthalate (PET) substrate (14 mm diameter, 0.2 mm thickness) was immersed in the above-prepared solution (5 ml) over a period of 2 hours at room temperature, so that a polymer membrane was formed on the PET substrate surface. Subsequently, the PET substrate coated with the polymer membrane was blood-contact tested by the method described above, and the polymer membrane surface was observed with a scanning electron microscope. The result is shown in FIG. 12.

Figure 12:
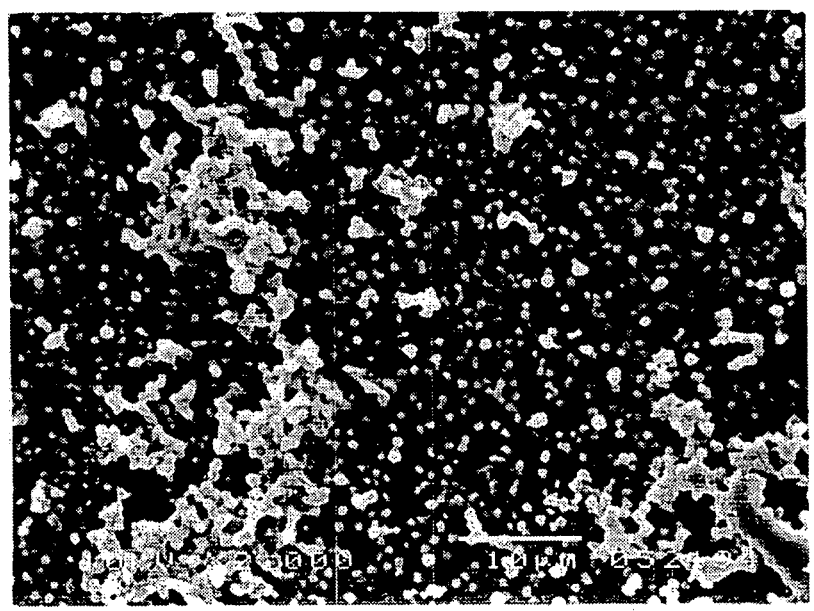
FIG. 12 is an electron micrograph (2000× magnification) showing a PA-0 membrane surface after contact with human PRP.

As is clear from FIG. 12, the polymer PA-0 membrane surface suffered adsorption of increased amounts of platelets and proteins, unlike with the PA-1 to PA-8 membrane surfaces shown in FIGS. 1 to 8.

Comparative Example 2

Synthesis of a Polyurethane Having no Phosphorylcholine Group and Blood-contact Test

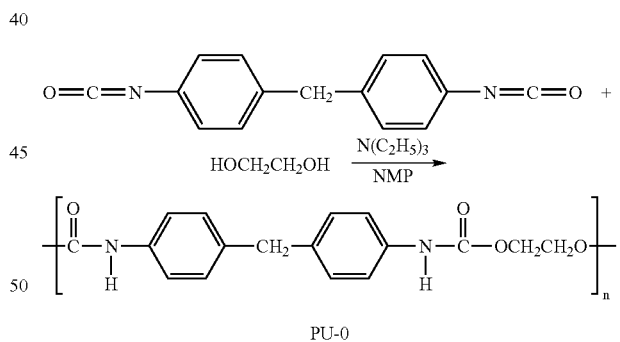

PU-0

<Synthesis of Polyurethane>

In an argon atmosphere, ethylene glycol (1.1 ml, 20 mmol) and triethylamine (0.3 ml) were dissolved in dry N-methylpyrrolidinone (20 ml) in a three-necked flask to give a solution. At room temperature, a solution of 4,4'-diphenylmethane diisocyanate (5.0 g, 20 mmol) in dry N-methylpyrrolidinone (20 ml) was slowly added dropwise to the solution. After the completion of the dropwise addition, the solution mixture was stirred for 2 hours at room temperature. After the reaction, the reaction solution was poured into excess ethanol to precipitate the obtained polymer. The precipitated polymer was filtered off and dried under reduced pressure to give 5.33 g of a polyurethane represented by the above formula PU-0 as white powder. The structure was identified by the $^1$H-NMR spectrum given below:

$^1$H-NMR, δ(400 MHz, DMSO-$d_6$, ppm): 3.78 (2H, s, —CH$_2$—), 4.29 (4H, s, —CH$_2$O—), 7.09 (8H, d, J=7.81 Hz, -Ph-), 7.36 (8H, d, J=8.30 Hz, -Ph-), 9.63 (2H, s, —NH—).

Gel permeation chromatography (solvent: dimethylformamide, standard: polystyrene) for PU-0 provided number-average molecular weight of 5.24×10$^4$ and weight-average molecular weight of 8.65×10$^4$. The glass transition temperature (softening point) of PU-0 was not observed in a temperature range of ambient to 300° C. by differential scanning calorimetry. Also, PU-0 was found to have similar solubility characteristics to those of PUU-1.

<Blood-contact Test>

The polymer PU-0 was dissolved in dimethylformamide to achieve 1.5 wt % concentration. A polyethyleneterephthalate (PET) substrate (14 mm diameter, 0.2 mm thickness) was immersed in the above-prepared solution (5 ml) for 2 hours at room temperature, so that a polymer membrane was formed on the PET substrate surface. Subsequently, the PET substrate coated with the polymer membrane was blood-contact tested by the method described above, and the polymer membrane surface was observed with a scanning electron microscope. The result is shown in FIG. 13.

Figure 9:
FIG. 9 is an electron micrograph (2000× magnification) showing a PUU-1 membrane surface after contact with human PRP.
Figure 10:
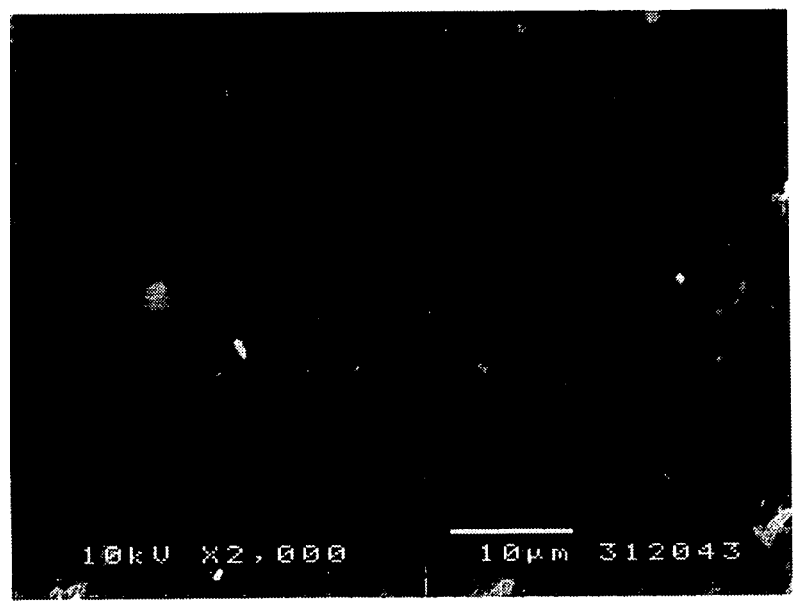
FIG. 10 is an electron micrograph (2000× magnification) showing a PUU-2 membrane surface after contact with human PRP.
Figure 11:
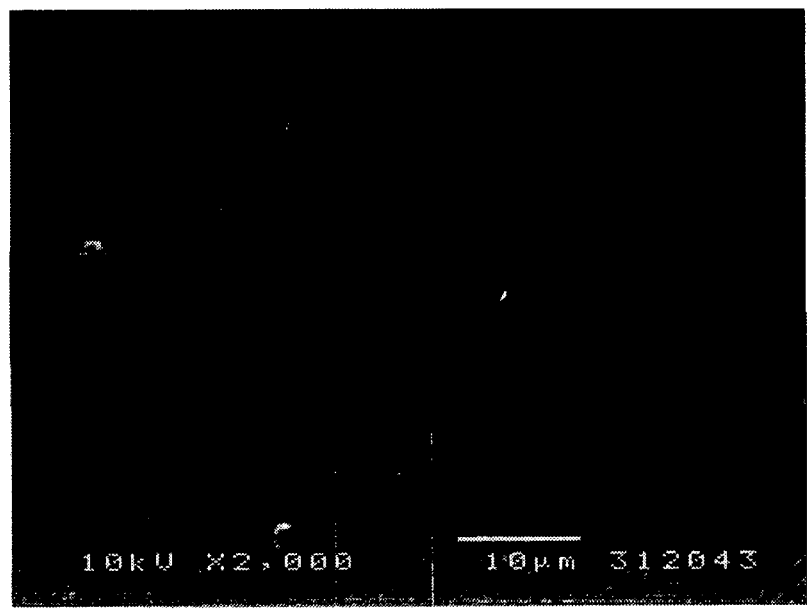
FIG. 11 is an electron micrograph (2000× magnification) showing a PUU-3 membrane surface after contact with human PRP.
Figure 13:
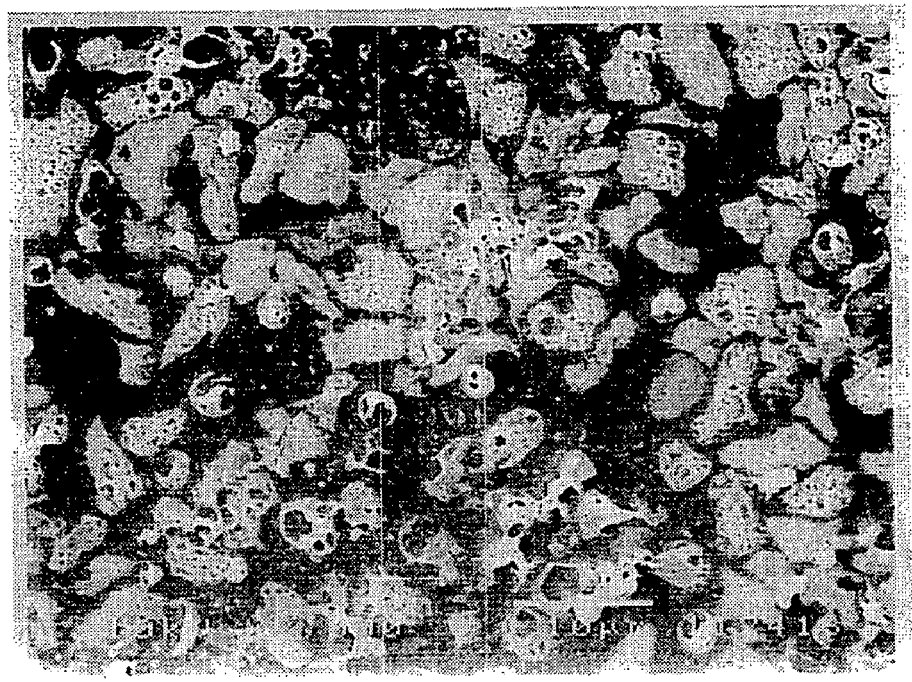
FIG. 13 is an electron micrograph (2000× magnification) showing a PU-0 membrane surface after contact with human PRP.

As is clear from FIG. 13, the polymer PU-0 membrane surface suffered adsorption of increased amounts of platelets and proteins, unlike with the PUU-1 to PUU-3 membrane surfaces shown in FIGS. 9 to 11.

INDUSTRIAL APPLICABILITY

The polymers according to the present invention are biocompatible materials having superior antithrombotic properties and capable of substantially restraining adsorption of biocomponents such as proteins. Accordingly, they are useful in artificial organs such as artificial blood vessels and other medical devices.

The invention claimed is:

1. A compound represented by the formula (I):

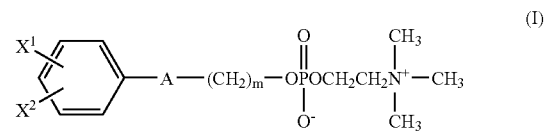

wherein X$^1$ and X$^2$ are both amino groups or both —COOR$^1$ groups where R$^1$'s may be the same or different from each other and are each a hydrogen atom or a carboxyl-protective group; A is a bond selected from a single bond, —O—, —COO—, —OOC—, —CONH—, —NH—, —NHCO—, —NR$^2$— and —CH$_2$O— where R$^2$ is an alkyl group having 1 to 6 carbon atoms; and m is an integer of 1 to 12.

2. The compound according to claim 1, wherein X$^1$ and X$^2$ are both amino groups.

3. The compound according to claim 1, wherein X$^1$ and X$^2$ are both —COOR$^1$ groups where R$^1$'s are both hydrogen atoms.

4. The compound according to claim 1, wherein X$^1$ and X$^2$ are both —COOR$^1$ groups where R$^1$'s may be the same or different from each other and are each an alkyl group having 1 to 6 carbon atoms, a substituted or unsubstituted arylmethyl group, a cyclic ether residue, an alkylsilyl group or an alkylphenylsilyl group.

5. The compound according to claim 2, wherein A is a —COO— group.

* * * * *